United States Patent
Nakanishi et al.

(10) Patent No.: US 12,359,227 B2
(45) Date of Patent: Jul. 15, 2025

(54) POLYPEPTIDES HAVING PULLULANASE ACTIVITY SUITABLE FOR USE IN LIQUEFACTION

(71) Applicant: Novozymes A/S, Bagsvaerd (DK)

(72) Inventors: Takashi Nakanishi, Chiba (JP); Aki Tomiki, Chiba (JP); Yuma Kurakata, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 817 days.

(21) Appl. No.: 17/440,477

(22) PCT Filed: Mar. 17, 2020

(86) PCT No.: PCT/EP2020/057218
§ 371 (c)(1),
(2) Date: Sep. 17, 2021

(87) PCT Pub. No.: WO2020/187883
PCT Pub. Date: Sep. 24, 2020

(65) Prior Publication Data
US 2022/0154226 A1 May 19, 2022

(30) Foreign Application Priority Data
Mar. 18, 2019 (EP) .................................... 19163366

(51) Int. Cl.
*C12P 7/06* (2006.01)
*C12N 9/44* (2006.01)

(52) U.S. Cl.
CPC .............. *C12P 7/06* (2013.01); *C12N 9/2457* (2013.01); *C12Y 302/01041* (2013.01)

(58) Field of Classification Search
None
See application file for complete search history.

(56) References Cited

U.S. PATENT DOCUMENTS

| | | | |
|---|---|---|---|
| 5,817,498 A | 10/1998 | Deweer et al. | |
| 6,074,854 A | 6/2000 | Deweer et al. | |
| 9,267,124 B2 * | 2/2016 | Matsui | C12P 19/20 |
| 9,765,316 B2 * | 9/2017 | Matsui | C12N 9/242 |
| 9,828,595 B2 * | 11/2017 | Matsui | C12Y 305/01001 |
| 10,472,617 B2 * | 11/2019 | Matsui | A23L 5/25 |
| 10,927,361 B2 * | 2/2021 | Ayabe | C12Y 304/21 |
| 11,220,679 B2 * | 1/2022 | Tsutsumi | C12N 9/2402 |
| 11,377,648 B2 * | 7/2022 | Namoto | C12N 15/52 |
| 11,427,811 B2 * | 8/2022 | Matsui | C12N 9/2428 |
| 11,447,763 B2 * | 9/2022 | Ayabe | C12N 9/58 |

FOREIGN PATENT DOCUMENTS

| | | |
|---|---|---|
| CN | 105960457 A | 9/2016 |
| CN | 107922933 A | 4/2018 |
| WO | 2009075682 A1 | 6/2009 |
| WO | 2015007639 A1 | 1/2015 |
| WO | 2015110473 A2 | 7/2015 |
| WO | 2017014974 A1 | 1/2017 |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7 (Year: 2011).*
Li et al. Biotechnol Bioeng. Jul. 2014;111(7):1273-87. Epub May 6, 2014. (Year: 2014).*
Chen et al, 2015, Enzyme Microb Technol 78, 74-83.
Duan et al, 2013, Appl Environ Microbiol 79(13), 4072-4077.

* cited by examiner

*Primary Examiner* — Christian L Fronda
(74) *Attorney, Agent, or Firm* — David A. Fazzolare

(57) ABSTRACT

The present invention relates to a variant pullulanase, having increased thermo-stability and/or increased thermo-activity compared to a parent pullulanase, comprising a substitution at least a one position selected from a position corresponding to positions 432, 486, 370, 17, 77, 103, 106, 107, 190, 196, 197, 262, 279, 283, 321, 367, 375, 382, 399, 401, 402, 411, 412, 434, 435, 443, 446, 459, 460, 479, 490, 498, 514, 529, 531, 533, 541, 545, 581, 583, 595, 649, 665, 688, 700, 709, 804, 811 of SEQ ID NO: 1, and optionally a deletion of one or more, e.g., all amino acids at positions 821, 822, 823, 824, 825, 826, 827, and 828, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5. Further aspect the present invention relates to a process for liquefying starch-containing material at a temperature above the initial gelatinization temperature using an alpha-amylase and a thermo-stable pullulanase of the invention.

25 Claims, No Drawings
Specification includes a Sequence Listing.

SEQUENCE LISTING

<160> NUMBER OF SEQ ID NOS: 17

<210> SEQ ID NO 1
<211> LENGTH: 828
<212> TYPE: PRT
<213> ORGANISM: Artificial
<220> FEATURE:
<223> OTHER INFORMATION: Synthetic construct

<400> SEQUENCE: 1

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Thr Gln Val Gly Leu Ile
    50                  55                  60

Val Arg Thr Asn Asp Trp Ser Gln Lys Asn Thr Ser Asp Asp Leu His
65                  70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
        115                 120                 125

Thr Asn Pro Met Thr Leu Ser Asp Gly Ser Ser Gly Phe Thr Val Thr
    130                 135                 140

Asp Lys Thr Thr Gly Glu Gln Ile Pro Val Thr Ala Ala Thr Asn Ala
145                 150                 155                 160

Asn Ser Ala Ser Ser Glu Gln Thr Asp Leu Val Gln Leu Thr Leu
            165                 170                 175

Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asn Leu Pro Arg
        195                 200                 205

Tyr Tyr Tyr Ser Gly Asn Asp Leu Gly Asn Val Tyr Ser Asn Lys Ala
    210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Gln Leu Glu Met Gln
                245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
        275                 280                 285

Ala Val Asp Pro Tyr Val Arg Ala Ile Ser Val Asn Ala Thr Arg Gly
    290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
                325                 330                 335

His Val Arg Asp Phe Ser Ile Asp Ala Asn Ser Gly Met Lys Asn Lys
            340                 345                 350

Gly Lys Tyr Leu Ala Phe Thr Glu His Gly Thr Lys Gly Pro Asp Asn

```
            355                 360                 365
Val Lys Thr Gly Ile Asp Ser Leu Lys Glu Leu Gly Ile Asn Ala Val
370                 375                 380

Gln Leu Gln Pro Ile Glu Glu Phe Asn Ser Ile Asp Glu Thr Gln Pro
385                 390                 395                 400

Asn Met Tyr Asn Trp Gly Tyr Asp Pro Arg Asn Tyr Asn Val Pro Glu
                405                 410                 415

Gly Ala Tyr Ala Thr Thr Pro Glu Gly Thr Ala Arg Ile Thr Gln Leu
            420                 425                 430

Lys Gln Leu Ile Gln Ser Ile His Lys Asp Arg Ile Ala Ile Asn Met
        435                 440                 445

Asp Val Val Tyr Asn His Thr Phe Ala Thr Gln Ile Ser Asp Phe Asp
450                 455                 460

Lys Ile Val Pro Glu Tyr Tyr Arg Thr Asp Asp Ala Gly Asn Tyr
465                 470                 475                 480

Thr Asn Gly Ser Gly Thr Gly Asn Glu Ile Ala Ala Glu Arg Pro Met
                485                 490                 495

Val Gln Lys Phe Ile Ile Asp Ser Leu Lys Tyr Trp Val Asn Glu Tyr
            500                 505                 510

His Ile Asp Gly Phe Arg Phe Asp Leu Met Ala Leu Leu Gly Lys Asp
        515                 520                 525

Thr Met Ser Lys Ala Ala Ser Glu Leu His Ala Ile Asn Pro Gly Ile
530                 535                 540

Ala Leu Tyr Gly Glu Pro Trp Thr Gly Gly Thr Ser Ala Leu Pro Glu
545                 550                 555                 560

Asp Gln Leu Leu Thr Lys Gly Ala Gln Lys Gly Met Gly Val Ala Val
                565                 570                 575

Phe Asn Asp Asn Leu Arg Asn Ala Leu Asp Gly Asn Val Phe Asp Ser
            580                 585                 590

Ser Ala Gln Gly Phe Ala Thr Gly Ala Thr Gly Leu Thr Asp Ala Ile
        595                 600                 605

Lys Asn Gly Val Glu Gly Ser Ile Asn Asp Phe Thr Ser Ser Pro Gly
610                 615                 620

Glu Thr Ile Asn Tyr Val Thr Ser His Asp Asn Tyr Thr Leu Trp Asp
625                 630                 635                 640

Lys Ile Ala Leu Ser Asn Pro Asn Asp Ser Glu Ala Asp Arg Ile Lys
                645                 650                 655

Met Asp Glu Leu Ala Gln Ala Val Val Met Thr Ser Gln Gly Val Pro
            660                 665                 670

Phe Met Gln Gly Gly Glu Glu Met Leu Arg Thr Lys Gly Gly Asn Asp
        675                 680                 685

Asn Ser Tyr Asn Ala Gly Asp Thr Val Asn Glu Phe Asp Trp Ser Arg
690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                725                 730                 735

Asn Ser His Leu Gln Phe Leu Asn Ser Pro Glu Asn Thr Val Ala Tyr
            740                 745                 750

Glu Leu Thr Asp His Val Asn Lys Asp Lys Trp Gly Asn Ile Ile Val
        755                 760                 765

Val Tyr Asn Pro Asn Lys Thr Ala Ala Thr Ile Asn Leu Pro Ser Gly
770                 775                 780
```

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
            805                 810                 815

Leu His Gln Glu Val Ser Pro Asp His Gly Lys Lys
            820                 825

<210> SEQ ID NO 2
<211> LENGTH: 2586
<212> TYPE: DNA
<213> ORGANISM: Artificial
<220> FEATURE:
<223> OTHER INFORMATION: Synthetic construct

<400> SEQUENCE: 2

| | |
|---|---|
| atgtccctaa tacgttctag gtataatcat tttgtcattc tttttactgt cgccataatg | 60 |
| tttctaacag tttgtttccc cgcttataaa gctttagcag attctacctc gacagaagtc | 120 |
| attgtgcatt atcatcgttt tgattctaac tatgcaaatt gggatctatg gatgtggcca | 180 |
| tatcaaccag ttaatggtaa tggagcagca tacgagtttt ctggaaagga tgattttggc | 240 |
| gttaaagcag atgttcaagt gcctggggat gatacacagg taggtctgat tgtccgtaca | 300 |
| aatgattgga gccaaaaaaa tacatcagac gatctccata ttgatctgac aaaggggcat | 360 |
| gaaatatgga ttgttcaggg ggatcccaat atttattaca atctgagtga tgcgcaggct | 420 |
| gcagcgactc caaaggtttc gaatgcgtat ttggataatg aaaaaacagt attggcaaag | 480 |
| ctaactaatc caatgacatt atcagatgga tcaagcggct ttacggttac agataaaaca | 540 |
| acagggaac aaattccagt taccgctgca acaaatgcga actcagcctc ctcgtctgag | 600 |
| cagacagact tggttcaatt gacgttagcc agtgcaccgg atgtttccca tacaatacaa | 660 |
| gtaggagcag ccggttatga agcagtcaat ctcataccac gaaatgtatt aaatttgcct | 720 |
| cgttattatt acagcggaaa tgatttaggt aacgtttatt caaataaggc aacgccttc | 780 |
| cgtgtatggg ctccaactgc ttcggatgtc caattacttt tatacaatag tgaaacagga | 840 |
| cctgtaacca aacagcttga atgcaaaag agtgataacg gtacatggaa actgaaggtc | 900 |
| cctggtaatc tgaaaaattg gtattatctc tatcaggtaa cggtgaatgg aagacacaa | 960 |
| acagccgttg accctatgt gcgtgctatt tcagtcaatg caacacgtgg tatgatagtc | 1020 |
| gatttagaag atacgaatcc tcctggatgg aaagaagatc atcaacagac acctgcgaac | 1080 |
| ccagtggatg aagtaatcta cgaagtgcat gtgcgtgatt tttcgattga tgctaattca | 1140 |
| ggcatgaaaa ataaagggaa atatcttgcc tttacagaac atggcacaaa aggccctgat | 1200 |
| aacgtgaaaa cgggtattga tagtttgaag gaattaggaa tcaatgctgt tcaattacag | 1260 |
| ccgattgaag aatttaacag cattgatgaa acccaaccaa atatgtataa ctgggggctat | 1320 |
| gacccaagaa actacaacgt ccctgaagga gcgtatgcaa ctacaccaga aggaacggct | 1380 |
| cgcattaccc agttaaagca actgattcaa agcattcata agatcggat tgctatcaat | 1440 |
| atggatgtgg tctataatca tacctttgcc acgcaaatct ctgacttcga taaaattgta | 1500 |
| ccagaatatt attaccgtac ggatgatgca ggtaattata ccaacggatc aggtactgga | 1560 |
| aatgaaatcg cagccgaaag gccaatggtt caaaaattta ttattgattc ccttaagtat | 1620 |
| tgggtcaatg agtatcatat tgacggcttc cgttttgact aatggcgct gcttggaaaa | 1680 |
| gacacgatgt cgaaagctgc ctcggagctt catgctatta atccaggaat tgcactttac | 1740 |
| ggtgagccat ggacgggtgg aacctctgca ctgccagaag atcagcttct gacaaaagga | 1800 |

```
gctcaaaaag gcatgggagt agcggtgttt aatgacaatt tacgaaacgc gttggacggc    1860
aatgtctttg attcttccgc tcaaggtttt gcgacaggtg caacaggctt aactgatgca    1920
attaagaatg gcgttgaggg gagtattaat gactttacct cttcaccagg tgagacaatt    1980
aactatgtca caagtcatga taactacacc ctttgggaca aaatagccct aagcaaccct    2040
aatgattccg aagcggatcg gattaaaatg gatgaactcg cacaagcagt tgttatgacc    2100
tcacaaggtg ttccattcat gcaaggcggg gaagaaatgc ttcgtacaaa aggcggcaac    2160
gacaatagtt ataatgcagg cgatacggtc aatgagtttg attggagcag gaaagctcaa    2220
tatccagatg ttttcaacta ttatagcggg ctaatccacc ttcgtcttga tcacccagcc    2280
ttccgcatga cgacagctaa tgaaatcaat agccacctcc aattcctaaa tagtccagag    2340
aacacagtgg cctatgaatt aactgatcat gttaataaag acaaatgggg aaatatcatt    2400
gttgtttata acccaaataa aactgcagca accattaatt tgccgagcgg gaaatgggca    2460
atcaatgcta cgagcggtaa ggtaggagaa tccacccttg gtcaagcaga gggaagtgtc    2520
caagtaccag gtatatctat gatgatcctt catcaagagg taagcccaga ccacggtaaa    2580
aagtaa                                                               2586

<210> SEQ ID NO 3
<211> LENGTH: 825
<212> TYPE: PRT
<213> ORGANISM: Artificial
<220> FEATURE:
<223> OTHER INFORMATION: Synthetic construct

<400> SEQUENCE: 3

Asp Ser Thr Ser Thr Glu Val Ile Val His Tyr His Arg Phe Asp Ser
1               5                   10                  15

Asn Tyr Ala Gly Trp Asp Leu Trp Met Trp Pro Lys Gly Gly Asn Gly
            20                  25                  30

Ala Ala Tyr Glu Phe Ser Gly Lys Asp Phe Gly Val Lys Ala Asp
        35                  40                  45

Val Gln Val Pro Gly Asn Pro Thr Gln Val Gly Leu Ile Val Arg Thr
    50                  55                  60

Asn Asp Trp Ser Gln Lys Asn Thr Ser Asp Asp Leu Tyr Ile Asp Leu
65                  70                  75                  80

Thr Lys Gly His Glu Ile Trp Ile Val Gln Gly Asp Pro Asn Ile Tyr
                85                  90                  95

Tyr Asn Leu Ser Asp Ala Gln Ala Ala Ala Thr Pro Lys Val Ser Asn
            100                 105                 110

Ala Tyr Leu Asp Asn Glu Lys Thr Val Leu Ala Lys Leu Thr Asn Pro
        115                 120                 125

Met Thr Leu Ser Asp Gly Ser Ser Gly Phe Thr Val Thr Asp Lys Thr
    130                 135                 140

Thr Gly Glu Gln Ile Pro Val Thr Ala Ala Thr Asn Ala Asn Ser Ala
145                 150                 155                 160

Ser Ser Ser Glu Gln Thr Asp Leu Val Gln Leu Thr Leu Ala Ser Ala
                165                 170                 175

Pro Asp Val Ser His Thr Ile Arg Val Gly Ala Ala Gly Tyr Glu Gly
            180                 185                 190

Val Thr Leu Ile Pro Arg Lys Val Leu Asn Leu Pro Arg Tyr Tyr Tyr
        195                 200                 205

Ser Gly Asn Asp Leu Gly Asn Val Tyr Ser Pro Lys Ala Thr Ala Phe
```

```
                    210                 215                 220
Arg Val Trp Ala Pro Thr Ala Ser Asp Val Gln Leu Leu Tyr Asn
225                 230                 235                 240

Ser Glu Thr Gly Pro Val Thr Lys Ala Leu Glu Met Arg Lys Ser Asp
                    245                 250                 255

Asn Gly Thr Trp Lys Leu Lys Val Pro Gly Asn Leu Lys Asn Trp Tyr
                260                 265                 270

Tyr Leu Tyr Gln Val Thr Val Asn Gly Lys Thr Gln Thr Ala Val Asp
            275                 280                 285

Pro Tyr Val Arg Ala Ile Ser Val Asn Ala Thr Arg Gly Met Ile Val
        290                 295                 300

Asp Leu Ala Lys Thr Asn Pro Pro Gly Trp Lys Glu Asp His Gln Gln
305                 310                 315                 320

Thr Pro Ala Asn Pro Val Asp Glu Val Ile Tyr Glu Val His Val Arg
                325                 330                 335

Asp Phe Ser Ile Asp Pro Asn Ser Gly Met Lys Asn Lys Gly Lys Tyr
                340                 345                 350

Leu Ala Phe Thr Glu His Gly Thr Lys Gly Pro Asp Gly Val Lys Thr
            355                 360                 365

Gly Ile Asp Ser Leu Lys Glu Leu Gly Ile Asn Ala Val Gln Leu Leu
        370                 375                 380

Pro Ile Glu Glu Phe Ala Ser Ile Asp Glu Thr Gln Pro Asn Ser Tyr
385                 390                 395                 400

Asn Trp Gly Tyr Asp Pro Arg Asn Tyr Asn Val Pro Glu Gly Ala Tyr
                405                 410                 415

Ala Thr Thr Pro Glu Gly Thr Ala Arg Ile Thr Glu Phe Lys Gln Leu
                420                 425                 430

Ile Gln Ser Ile His Lys Asp Arg Ile Ala Ile Asn Met Asp Val Val
            435                 440                 445

Tyr Asn His Thr Trp Ala Thr Gly Val Ser Asp Phe Asp Lys Ile Val
        450                 455                 460

Pro Glu Tyr Tyr Tyr Arg Thr Asp Asp Ala Gly His Tyr Thr Asn Gly
465                 470                 475                 480

Ser Gly Thr Gly Asn Glu Ile Ala Ala Glu Arg Pro Met Val Gln Lys
                485                 490                 495

Phe Ile Ile Asp Ser Leu Lys Tyr Trp Val Asn Glu Tyr His Val Asp
                500                 505                 510

Gly Phe Arg Phe Asp Leu Met Ala Leu Leu Gly Lys Asp Thr Met Ser
            515                 520                 525

Lys Ala Ala Ser Glu Leu His Ala Ile Asn Pro Gly Ile Ala Leu Tyr
        530                 535                 540

Gly Glu Pro Trp Thr Gly Gly Thr Ser Ala Leu Pro Arg Asp Gln Leu
545                 550                 555                 560

Leu Thr Lys Gly Ala Gln Lys Gly Met Gly Val Ala Val Phe Asn Asp
                565                 570                 575

Asn Leu Arg Asn Ala Leu Ser Gly Asn Val Phe Asp Ser Ser Ala Gln
                580                 585                 590

Gly Phe Ala Thr Gly Ala Thr Gly Leu Thr Asp Ala Ile Lys Arg Gly
            595                 600                 605

Val Glu Gly Ser Ile Asn Asp Phe Thr Ser Ser Pro Ser Glu Thr Ile
        610                 615                 620

Asn Tyr Val Ser Cys His Asp Asn Tyr Thr Leu Trp Asp Lys Ile Ala
625                 630                 635                 640
```

Leu Ser Asn Pro Asn Asp Ser Glu Ala Asp Arg Ile Lys Met Asp Glu
            645                 650                 655

Leu Ala Gln Ala Val Val Met Thr Ser Gln Gly Val Pro Phe Met Gln
            660                 665                 670

Gly Gly Glu Glu Met Leu Arg Thr Lys Gly Gly Asn Asp Asn Ser Tyr
            675                 680                 685

Asn Ala Gly Asp Thr Val Asn Arg Phe Asp Trp Ser Arg Lys Ala Gln
            690                 695                 700

Tyr Pro Asp Val Phe Asn Tyr Tyr Ser Gly Leu Ile His Leu Arg Leu
705                 710                 715                 720

Asp His Pro Ala Phe Arg Met Thr Thr Ala Asn Glu Ile Asn Ser His
            725                 730                 735

Leu Gln Phe Leu Asn Ser Pro Glu Asn Thr Val Ala Tyr Glu Leu Thr
            740                 745                 750

Asp His Val Asn Lys Asp Lys Trp Gly Asn Ile Ile Val Val Tyr Asn
            755                 760                 765

Pro Asn Lys Thr Ala Ala Thr Ile Asn Leu Pro Ser Gly Lys Trp Ala
            770                 775                 780

Ile Asn Ala Thr Ser Gly Lys Val Gly Glu Arg Thr Leu Gly Gln Ala
785                 790                 795                 800

Glu Gly Ser Val Gln Val Pro Gly Ile Ser Met Met Ile Leu His Gln
            805                 810                 815

Glu Val Ser Pro Asp His Gly Lys Lys
            820                 825

<210> SEQ ID NO 4
<211> LENGTH: 828
<212> TYPE: PRT
<213> ORGANISM: Artificial
<220> FEATURE:
<223> OTHER INFORMATION: Synthetic construct

<400> SEQUENCE: 4

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
            35                  40                  45

Lys Ala Asp Val Gln Val Pro Gly Asp Thr Gln Val Gly Leu Ile
            50                  55                  60

Val Arg Thr Asn Asp Trp Ser Gln Lys Asn Thr Ser Asp Asp Leu His
65              70                  75                  80

Ile Asp Leu Thr Lys Gly His Glu Ile Trp Ile Val Gln Gly Asp Pro
            85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
            115                 120                 125

Thr Asn Pro Met Thr Leu Ser Asp Gly Ser Ser Gly Phe Thr Val Thr
            130                 135                 140

Asp Lys Thr Thr Gly Glu Gln Ile Pro Val Thr Ala Ala Thr Asn Ala
145                 150                 155                 160

Asn Ser Ala Ser Ser Ser Glu Gln Thr Asp Leu Val Gln Leu Thr Leu
            165                 170                 175

Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asn Leu Pro Arg
            195                 200                 205

Tyr Tyr Tyr Ser Gly Asn Asp Leu Gly Asn Val Tyr Ser Pro Lys Ala
210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Ala Leu Glu Met Arg
            245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
            275                 280                 285

Ala Val Asp Pro Tyr Val Arg Ala Ile Ser Val Asn Ala Thr Arg Gly
            290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
            325                 330                 335

His Val Arg Asp Phe Ser Ile Asp Ala Asn Ser Gly Met Lys Asn Lys
            340                 345                 350

Gly Lys Tyr Leu Ala Phe Thr Glu His Gly Thr Lys Gly Pro Asp Gly
            355                 360                 365

Val Lys Thr Gly Ile Asp Ser Leu Lys Glu Leu Gly Ile Asn Ala Val
            370                 375                 380

Gln Leu Gln Pro Ile Glu Glu Phe Ala Ser Ile Asp Glu Thr Gln Pro
385                 390                 395                 400

Asn Met Tyr Asn Trp Gly Tyr Asp Pro Arg Asn Tyr Asn Val Pro Glu
            405                 410                 415

Gly Ala Tyr Ala Thr Thr Pro Glu Gly Thr Ala Arg Ile Thr Glu Phe
            420                 425                 430

Lys Gln Leu Ile Gln Ser Ile His Lys Asp Arg Ile Ala Ile Asn Met
            435                 440                 445

Asp Val Val Tyr Asn His Thr Phe Ala Thr Gln Ile Ser Asp Phe Asp
450                 455                 460

Lys Ile Val Pro Glu Tyr Tyr Tyr Arg Thr Asp Asp Ala Gly Asn Tyr
465                 470                 475                 480

Thr Asn Gly Ser Gly Thr Gly Asn Glu Ile Ala Ala Glu Arg Pro Met
            485                 490                 495

Val Gln Lys Phe Ile Ile Asp Ser Leu Lys Tyr Trp Val Asn Glu Tyr
            500                 505                 510

His Ile Asp Gly Phe Arg Phe Asp Leu Met Ala Leu Leu Gly Lys Asp
            515                 520                 525

Thr Met Ser Lys Ala Ala Ser Glu Leu His Ala Ile Asn Pro Gly Ile
530                 535                 540

Ala Leu Tyr Gly Glu Pro Trp Thr Gly Gly Thr Ser Ala Leu Pro Glu
545                 550                 555                 560

Asp Gln Leu Leu Thr Lys Gly Ala Gln Lys Gly Met Gly Val Ala Val
            565                 570                 575

Phe Asn Asp Asn Leu Arg Asn Ala Leu Asp Gly Asn Val Phe Asp Ser
            580                 585                 590

-continued

```
Ser Ala Gln Gly Phe Ala Thr Gly Ala Thr Gly Leu Thr Asp Ala Ile
            595                 600                 605

Lys Arg Gly Val Glu Gly Ser Ile Asn Asp Phe Thr Ser Ser Pro Ser
610                 615                 620

Glu Thr Ile Asn Tyr Val Ser Cys His Asp Asn Tyr Thr Leu Trp Asp
625                 630                 635                 640

Lys Ile Ala Leu Ser Asn Pro Asn Asp Ser Glu Ala Asp Arg Ile Lys
            645                 650                 655

Met Asp Glu Leu Ala Gln Ala Val Val Met Thr Ser Gln Gly Val Pro
        660                 665                 670

Phe Met Gln Gly Gly Glu Glu Met Leu Arg Thr Lys Gly Gly Asn Asp
        675                 680                 685

Asn Ser Tyr Asn Ala Gly Asp Thr Val Asn Glu Phe Asp Trp Ser Arg
    690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
            725                 730                 735

Asn Ser His Leu Gln Phe Leu Asn Ser Pro Glu Asn Thr Val Ala Tyr
        740                 745                 750

Glu Leu Thr Asp His Val Asn Lys Asp Lys Trp Gly Asn Ile Ile Val
        755                 760                 765

Val Tyr Asn Pro Asn Lys Thr Ala Ala Thr Ile Asn Leu Pro Ser Gly
    770                 775                 780

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
            805                 810                 815

Leu His Gln Glu Val Ser Pro Asp His Gly Lys Lys
        820                 825

<210> SEQ ID NO 5
<211> LENGTH: 828
<212> TYPE: PRT
<213> ORGANISM: Artificial
<220> FEATURE:
<223> OTHER INFORMATION: Synthetic construct

<400> SEQUENCE: 5

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Thr Gln Val Gly Leu Ile
    50                  55                  60

Val Arg Thr Asn Asp Trp Ser Gln Lys Asn Thr Ser Asp Leu Tyr
65                  70                  75                  80

Ile Asp Leu Thr Lys Gly His Glu Ile Trp Ile Val Gln Gly Asp Pro
            85                  90                  95

Asn Ile Tyr Tyr Asn Leu Ser Asp Ala Gln Ala Ala Thr Pro Lys
        100                 105                 110

Val Ser Asn Ala Tyr Leu Asp Asn Glu Lys Thr Val Leu Ala Lys Leu
    115                 120                 125
```

```
Thr Asn Pro Met Thr Leu Ser Asp Gly Ser Ser Gly Phe Thr Val Thr
130                 135                 140

Asp Lys Thr Thr Gly Glu Gln Ile Pro Val Thr Ala Ala Thr Asn Ala
145                 150                 155                 160

Asn Ser Ala Ser Ser Ser Glu Gln Thr Asp Leu Val Gln Leu Thr Leu
                165                 170                 175

Ala Ser Ala Pro Asp Val Ser His Thr Ile Arg Val Gly Ala Ala Gly
            180                 185                 190

Tyr Glu Ala Val Asn Leu Ile Pro Arg Asn Val Leu Asn Leu Pro Arg
        195                 200                 205

Tyr Tyr Tyr Ser Gly Asn Asp Leu Gly Asn Val Tyr Ser Pro Lys Ala
    210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Ala Leu Glu Met Arg
                245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
        275                 280                 285

Ala Val Asp Pro Tyr Val Arg Ala Ile Ser Val Asn Ala Thr Arg Gly
    290                 295                 300

Met Ile Val Asp Leu Ala Lys Thr Asn Pro Pro Gly Trp Lys Glu Asp
305                 310                 315                 320

His Gln Gln Thr Pro Ala Asn Pro Val Asp Glu Val Ile Tyr Glu Val
                325                 330                 335

His Val Arg Asp Phe Ser Ile Asp Ala Asn Ser Gly Met Lys Asn Lys
            340                 345                 350

Gly Lys Tyr Leu Ala Phe Thr Glu His Gly Thr Lys Gly Pro Asp Gly
        355                 360                 365

Val Lys Thr Gly Ile Asp Ser Leu Lys Glu Leu Gly Ile Asn Ala Val
    370                 375                 380

Gln Leu Leu Pro Ile Glu Glu Phe Ala Ser Ile Asp Glu Thr Gln Pro
385                 390                 395                 400

Asn Met Tyr Asn Trp Gly Tyr Asp Pro Arg Asn Tyr Asn Val Pro Glu
                405                 410                 415

Gly Ala Tyr Ala Thr Thr Pro Glu Gly Thr Ala Arg Ile Thr Glu Phe
            420                 425                 430

Lys Gln Leu Ile Gln Ser Ile His Lys Asp Arg Ile Ala Ile Asn Met
        435                 440                 445

Asp Val Val Tyr Asn His Thr Phe Ala Thr Gly Ile Ser Asp Phe Asp
450                 455                 460

Lys Ile Val Pro Glu Tyr Tyr Arg Thr Asp Asp Ala Gly Asn Tyr
465                 470                 475                 480

Thr Asn Gly Ser Gly Thr Gly Asn Glu Ile Ala Ala Glu Arg Pro Met
                485                 490                 495

Val Gln Lys Phe Ile Ile Asp Ser Leu Lys Tyr Trp Val Asn Glu Tyr
            500                 505                 510

His Ile Asp Gly Phe Arg Phe Asp Leu Met Ala Leu Leu Gly Lys Asp
        515                 520                 525

Thr Met Ser Lys Ala Ala Ser Glu Leu His Ala Ile Asn Pro Gly Ile
    530                 535                 540

Ala Leu Tyr Gly Glu Pro Trp Thr Gly Gly Thr Ser Ala Leu Pro Glu
```

```
545                 550                 555                 560
Asp Gln Leu Leu Thr Lys Gly Ala Gln Lys Gly Met Gly Val Ala Val
                565                 570                 575

Phe Asn Asp Asn Leu Arg Asn Ala Leu Asp Gly Asn Val Phe Asp Ser
                580                 585                 590

Ser Ala Gln Gly Phe Ala Thr Gly Ala Thr Gly Leu Thr Asp Ala Ile
                595                 600                 605

Lys Arg Gly Val Glu Gly Ser Ile Asn Asp Phe Thr Ser Ser Pro Ser
                610                 615                 620

Glu Thr Ile Asn Tyr Val Ser Cys His Asp Asn Tyr Thr Leu Trp Asp
625                 630                 635                 640

Lys Ile Ala Leu Ser Asn Pro Asn Asp Ser Glu Ala Asp Arg Ile Lys
                645                 650                 655

Met Asp Glu Leu Ala Gln Ala Val Val Met Thr Ser Gln Gly Val Pro
                660                 665                 670

Phe Met Gln Gly Gly Glu Glu Met Leu Arg Thr Lys Gly Gly Asn Asp
                675                 680                 685

Asn Ser Tyr Asn Ala Gly Asp Thr Val Asn Glu Phe Asp Trp Ser Arg
                690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                725                 730                 735

Asn Ser His Leu Gln Phe Leu Asn Ser Pro Glu Asn Thr Val Ala Tyr
                740                 745                 750

Glu Leu Thr Asp His Val Asn Lys Asp Lys Trp Gly Asn Ile Ile Val
                755                 760                 765

Val Tyr Asn Pro Asn Lys Thr Ala Ala Thr Ile Asn Leu Pro Ser Gly
                770                 775                 780

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
                805                 810                 815

Leu His Gln Glu Val Ser Pro Asp His Gly Lys Lys
                820                 825

<210> SEQ ID NO 6
<211> LENGTH: 484
<212> TYPE: PRT
<213> ORGANISM: Bacillus stearothermophilus

<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
                35                  40                  45

Gly Thr Ser Arg Ser Asp Val Gly Tyr Gly Val Tyr Asp Leu Tyr Asp
                50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95
```

```
Gln Val Tyr Ala Asp Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys

<210> SEQ ID NO 7
<211> LENGTH: 177
<212> TYPE: PRT
<213> ORGANISM: Thermoascus aurantiacus
```

<400> SEQUENCE: 7

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
            35                  40                  45

Ser Ser Thr Arg Gln Thr Val Ala Ala Arg Leu Arg Ala Val Ala Arg
50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
                100                 105                 110

Leu Thr Ser Thr Cys His Ala Gln Asp Gln Ala Thr Thr Ala Leu His
            115                 120                 125

Glu Phe Thr His Ala Pro Gly Val Tyr Ser Pro Gly Thr Asp Asp Leu
130                 135                 140

Ala Tyr Gly Tyr Gln Ala Ala Met Gly Leu Ser Ser Gln Ala Val
145                 150                 155                 160

Met Asn Ala Asp Thr Tyr Ala Leu Tyr Ala Asn Ala Ile Tyr Leu Gly
                165                 170                 175

Cys

<210> SEQ ID NO 8
<211> LENGTH: 413
<212> TYPE: PRT
<213> ORGANISM: Pyrococcus furiosus

<400> SEQUENCE: 8

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
            115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

```
Ser Pro Ala Ala Ala Ser Lys Val Ile Thr Val Gly Ala Val Asp Lys
            180                 185                 190

Tyr Asp Val Ile Thr Ser Phe Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
        290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Asp Phe Glu Lys Val Gly Tyr Tyr Asn Pro Thr Asp Gly Thr Trp Thr
        370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro
                405                 410

<210> SEQ ID NO 9
<211> LENGTH: 325
<212> TYPE: PRT
<213> ORGANISM: Palaeococcus ferrophilus

<400> SEQUENCE: 9

Gly Lys Pro Lys Pro Ser Gln Pro Pro Gln Glu Val Pro Trp Gly Ile
1               5                   10                  15

Glu Arg Val Lys Ala Pro Ser Val Trp Ser Thr Thr Asp Gly Ser Ser
            20                  25                  30

Asn Gly Val Ile Gln Val Ala Ile Leu Asp Thr Gly Ile Asp Tyr Asp
        35                  40                  45

His Pro Asp Leu Ala Ala Asn Leu Ala Trp Gly Val Ser Thr Leu Arg
    50                  55                  60

Gly Arg Val Ser Thr Lys Pro Lys Asp Tyr Arg Asp Gln Asn Gly His
65                  70                  75                  80

Gly Thr His Val Ala Gly Thr Ile Ala Leu Asn Asn Asp Ile Gly
                85                  90                  95

Val Val Gly Val Ala Pro Gly Val Gln Ile Tyr Ala Ile Arg Val Leu
                100                 105                 110

Asp Ala Ser Gly Arg Gly Ser Tyr Ser Asp Ile Ala Ile Gly Ile Glu
        115                 120                 125

Gln Ala Ile Leu Gly Pro Asp Gly Val Ala Asp Lys Asp Gly Asp Gly
    130                 135                 140
```

```
Ile Ile Ala Gly Asp Pro Asp Asp Ala Glu Val Ile Ser Met
145                 150                 155                 160

Ser Leu Gly Gly Ser Ala Asp Ser Tyr Leu His Asp Met Ile Ile
        165                 170                 175

Gln Ala Tyr Asn Ala Gly Ile Val Ile Val Ala Ser Gly Asn Glu
            180                 185                 190

Gly Ala Ser Ser Pro Ser Tyr Pro Ala Ala Tyr Pro Glu Val Ile Ala
        195                 200                 205

Val Gly Ala Ser Asp Ile Asn Asp Asn Ile Ala Ser Phe Ser Asn Arg
        210                 215                 220

Gln Pro Glu Val Ser Ala Pro Gly Val Asp Val Leu Ser Thr Tyr Pro
225                 230                 235                 240

Asp Asp Thr Tyr Lys Thr Leu Ser Gly Thr Ser Met Ala Thr Pro His
                245                 250                 255

Val Ser Gly Val Val Ala Leu Ile Gln Ala Ala His Phe Asn Lys Tyr
            260                 265                 270

Gly Thr Ile Leu Pro Val Gly Thr Phe Asp Asp Met Ser Lys Asn Thr
        275                 280                 285

Val Arg Gly Ile Leu His Ile Thr Ala Asp Asp Leu Gly Ser Pro Gly
        290                 295                 300

Trp Asp Val Asp Tyr Gly Tyr Gly Ile Val Arg Ala Asp Leu Ala Val
305                 310                 315                 320

Gln Ala Ala Leu Gly
                325

<210> SEQ ID NO 10
<211> LENGTH: 598
<212> TYPE: PRT
<213> ORGANISM: Talaromyces emersonii

<400> SEQUENCE: 10

Arg Ala Pro Val Ala Ala Arg Ala Thr Gly Ser Leu Asp Ser Phe Leu
1               5                   10                  15

Ala Thr Glu Thr Pro Ile Ala Leu Gln Gly Val Leu Asn Asn Ile Gly
            20                  25                  30

Pro Asn Gly Ala Asp Val Ala Gly Ala Ser Ala Gly Ile Val Val Ala
        35                  40                  45

Ser Pro Ser Arg Ser Asp Pro Asn Tyr Phe Tyr Ser Trp Thr Arg Asp
    50                  55                  60

Ala Ala Leu Thr Ala Lys Tyr Leu Val Asp Ala Phe Ile Ala Gly Asn
65                  70                  75                  80

Lys Asp Leu Glu Gln Thr Ile Gln Gln Tyr Ile Ser Ala Gln Ala Lys
                85                  90                  95

Val Gln Thr Ile Ser Asn Pro Ser Gly Asp Leu Ser Thr Gly Gly Leu
            100                 105                 110

Gly Glu Pro Lys Phe Asn Val Asn Glu Thr Ala Phe Thr Gly Pro Trp
        115                 120                 125

Gly Arg Pro Gln Arg Asp Gly Pro Ala Leu Arg Ala Thr Ala Leu Ile
    130                 135                 140

Ala Tyr Ala Asn Tyr Leu Ile Asp Asn Gly Glu Ala Ser Thr Ala Asp
145                 150                 155                 160

Glu Ile Ile Trp Pro Ile Val Gln Asn Asp Leu Ser Tyr Ile Thr Gln
                165                 170                 175

Tyr Trp Asn Ser Ser Thr Phe Asp Leu Trp Glu Glu Val Glu Gly Ser
```

```
            180                 185                 190
Ser Phe Phe Thr Thr Ala Val Gln His Arg Ala Leu Val Glu Gly Asn
            195                 200                 205
Ala Leu Ala Thr Arg Leu Asn His Thr Cys Ser Asn Cys Val Ser Gln
            210                 215                 220
Ala Pro Gln Val Leu Cys Phe Leu Gln Ser Tyr Trp Thr Gly Ser Tyr
225                 230                 235                 240
Val Leu Ala Asn Phe Gly Gly Ser Gly Arg Ser Gly Lys Asp Val Asn
                245                 250                 255
Ser Ile Leu Gly Ser Ile His Thr Phe Asp Pro Ala Gly Gly Cys Asp
                260                 265                 270
Asp Ser Thr Phe Gln Pro Cys Ser Ala Arg Ala Leu Ala Asn His Lys
                275                 280                 285
Val Val Thr Asp Ser Phe Arg Ser Ile Tyr Ala Ile Asn Ser Gly Ile
            290                 295                 300
Ala Glu Gly Ser Ala Val Ala Val Gly Arg Tyr Pro Glu Asp Val Tyr
305                 310                 315                 320
Gln Gly Gly Asn Pro Trp Tyr Leu Ala Thr Ala Ala Ala Glu Gln
                325                 330                 335
Leu Tyr Asp Ala Ile Tyr Gln Trp Lys Lys Ile Gly Ser Ile Ser Ile
                340                 345                 350
Thr Asp Val Ser Leu Pro Phe Phe Gln Asp Ile Tyr Pro Ser Ala Ala
                355                 360                 365
Val Gly Thr Tyr Asn Ser Gly Ser Thr Thr Phe Asn Asp Ile Ile Ser
            370                 375                 380
Ala Val Gln Thr Tyr Gly Asp Gly Tyr Leu Ser Ile Val Glu Lys Tyr
385                 390                 395                 400
Thr Pro Ser Asp Gly Ser Leu Thr Glu Gln Phe Ser Arg Thr Asp Gly
                405                 410                 415
Thr Pro Leu Ser Ala Ser Ala Leu Thr Trp Ser Tyr Ala Ser Leu Leu
                420                 425                 430
Thr Ala Ser Ala Arg Arg Gln Ser Val Val Pro Ala Ser Trp Gly Glu
                435                 440                 445
Ser Ser Ala Ser Ser Val Pro Ala Val Cys Ser Ala Thr Ser Ala Thr
            450                 455                 460
Gly Pro Tyr Ser Thr Ala Thr Asn Thr Val Trp Pro Ser Ser Gly Ser
465                 470                 475                 480
Gly Ser Ser Thr Thr Thr Ser Ser Ala Pro Cys Thr Thr Pro Thr Ser
                485                 490                 495
Val Ala Val Thr Phe Asp Glu Ile Val Ser Thr Ser Tyr Gly Glu Thr
                500                 505                 510
Ile Tyr Leu Ala Gly Ser Ile Pro Glu Leu Gly Asn Trp Ser Thr Ala
                515                 520                 525
Ser Ala Ile Pro Leu Arg Ala Asp Ala Tyr Thr Asn Ser Asn Pro Leu
                530                 535                 540
Trp Tyr Val Thr Val Asn Leu Pro Pro Gly Thr Ser Phe Glu Tyr Lys
545                 550                 555                 560
Phe Phe Lys Asn Gln Thr Asp Gly Thr Ile Val Trp Glu Asp Asp Pro
                565                 570                 575
Asn Arg Ser Tyr Thr Val Pro Ala Tyr Cys Gly Gln Thr Thr Ala Ile
                580                 585                 590
Leu Asp Asp Ser Trp Gln
                595
```

<210> SEQ ID NO 11
<211> LENGTH: 555
<212> TYPE: PRT
<213> ORGANISM: Pycnoporus sanguinea

<400> SEQUENCE: 11

```
Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
            20                  25                  30

Gly Ala Lys Ala Gly Ile Val Val Ala Ser Pro Ser Thr Glu Asn Pro
        35                  40                  45

Asp Tyr Leu Tyr Thr Trp Thr Arg Asp Ser Ser Leu Val Phe Lys Leu
    50                  55                  60

Leu Ile Asp Gln Phe Thr Ser Gly Asp Thr Ser Leu Arg Gly Leu
65                  70                  75                  80

Ile Asp Asp Phe Thr Ser Ala Glu Ala Ile Leu Gln Gln Val Ser Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Gly Ala Trp Gly Arg Pro Gln Arg Asp
        115                 120                 125

Gly Pro Ala Leu Arg Ala Thr Ser Ile Ile Arg Tyr Ala Asn Trp Leu
    130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Phe Phe Thr Thr Ala
            180                 185                 190

Val Gln His Arg Ala Leu Arg Glu Gly Ala Thr Phe Ala Ser Arg Ile
        195                 200                 205

Gly Gln Ser Ser Val Val Ser Gly Tyr Thr Thr Gln Ala Asp Asn Leu
    210                 215                 220

Leu Cys Phe Leu Gln Ser Tyr Trp Asn Pro Ser Gly Gly Tyr Val Thr
225                 230                 235                 240

Ala Asn Thr Gly Gly Gly Arg Ser Gly Lys Asp Ser Asn Thr Val Leu
                245                 250                 255

Thr Ser Ile His Thr Phe Asp Pro Ala Ala Gly Cys Asp Ala Ala Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Thr Ile Asn Asn Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
        355                 360                 365

Tyr Ser Ala Ser Ser Ser Thr Tyr Ala Thr Leu Thr Ser Ala Ile Arg
```

```
              370                 375                 380
Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
                405                 410                 415

Ser Ala Val Asp Leu Thr Trp Ser Tyr Ala Ala Ala Leu Thr Ala Phe
                420                 425                 430

Ala Ala Arg Glu Gly Lys Thr Tyr Gly Ser Trp Gly Ala Ala Gly Leu
                435                 440                 445

Thr Val Pro Ala Ser Cys Ser Gly Gly Gly Ala Thr Val Ala Val
                450                 455                 460

Thr Phe Asn Val Gln Ala Thr Thr Val Phe Gly Glu Asn Ile Tyr Ile
465                 470                 475                 480

Thr Gly Ser Val Ala Ala Leu Gln Asn Trp Ser Pro Asn Ala Leu
                485                 490                 495

Ile Leu Ser Ala Ala Asn Tyr Pro Thr Trp Ser Ile Thr Val Asn Leu
                500                 505                 510

Pro Ala Asn Thr Val Val Gln Tyr Lys Tyr Ile Arg Lys Phe Asn Gly
                515                 520                 525

Gln Val Thr Trp Glu Ser Asp Pro Asn Asn Gln Ile Thr Thr Pro Ser
                530                 535                 540

Gly Gly Ser Phe Thr Gln Asn Asp Val Trp Arg
545                 550                 555

<210> SEQ ID NO 12
<211> LENGTH: 556
<212> TYPE: PRT
<213> ORGANISM: Gloeophyllum sepiarium

<400> SEQUENCE: 12

Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
                20                  25                  30

Ser Ala Gly Val Val Ala Ser Pro Ser Thr Ser Asp Pro Asp Tyr
            35                  40                  45

Trp Tyr Thr Trp Thr Arg Asp Ser Ser Leu Val Phe Lys Ser Leu Ile
        50                  55                  60

Asp Gln Tyr Thr Thr Gly Ile Asp Ser Thr Ser Ser Leu Arg Thr Leu
65              70                  75                  80

Ile Asp Asp Phe Val Thr Ala Glu Ala Asn Leu Gln Gln Val Ser Asn
                85                  90                  95

Pro Ser Gly Thr Leu Thr Thr Gly Gly Leu Gly Glu Pro Lys Phe Asn
                100                 105                 110

Val Asp Glu Thr Ala Phe Thr Gly Ala Trp Gly Arg Pro Gln Arg Asp
            115                 120                 125

Gly Pro Ala Leu Arg Ser Thr Ala Leu Ile Thr Tyr Gly Asn Trp Leu
        130                 135                 140

Leu Ser Asn Gly Asn Thr Ser Tyr Val Thr Ser Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Ser Phe Phe Thr Thr Ala
            180                 185                 190
```

```
Val Gln His Arg Ala Leu Arg Glu Gly Ala Ala Phe Ala Thr Ala Ile
            195                 200                 205

Gly Gln Thr Ser Gln Val Ser Ser Tyr Thr Thr Gln Ala Asp Asn Leu
    210                 215                 220

Leu Cys Phe Leu Gln Ser Tyr Trp Asn Pro Ser Gly Gly Tyr Ile Thr
225                 230                 235                 240

Ala Asn Thr Gly Gly Arg Ser Gly Lys Asp Ala Asn Thr Leu Leu
                245                 250                 255

Ala Ser Ile His Thr Tyr Asp Pro Ser Ala Gly Cys Asp Ala Ala Thr
                260                 265                 270

Phe Gln Pro Cys Ser Asp Lys Ala Leu Ser Asn Leu Lys Val Tyr Val
                275                 280                 285

Asp Ser Phe Arg Ser Val Tyr Ser Ile Asn Ser Gly Val Ala Ser Asn
                290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
                340                 345                 350

Ser Leu Ala Phe Phe Gln Gln Phe Ser Ser Gly Val Thr Ala Gly Thr
                355                 360                 365

Tyr Ser Ser Ser Ser Thr Tyr Ser Thr Leu Thr Ser Ala Ile Lys
                370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Ala Gly Leu
                435                 440                 445

Thr Val Pro Ser Ser Cys Ser Gly Asn Ser Gly Pro Thr Val Ala
450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
                500                 505                 510

Leu Pro Ala Ser Thr Ala Ile Glu Tyr Lys Tyr Ile Arg Lys Asn Asn
                515                 520                 525

Gly Ala Val Thr Trp Glu Ser Asp Pro Asn Asn Ser Ile Thr Thr Pro
                530                 535                 540

Ala Ser Gly Ser Thr Thr Glu Asn Asp Thr Trp Arg
545                 550                 555

<210> SEQ ID NO 13
<211> LENGTH: 559
<212> TYPE: PRT
<213> ORGANISM: Gloeophyllum trabeum

<400> SEQUENCE: 13

Gln Ser Val Asp Ser Tyr Val Gly Ser Glu Gly Pro Ile Ala Lys Ala
1               5                   10                  15
```

```
Gly Val Leu Ala Asn Ile Gly Pro Asn Gly Ser Lys Ala Ser Gly Ala
            20                  25                  30

Ala Ala Gly Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                      70                  75                  80

Ile Asp Ser Phe Val Ile Ala Glu Ala Asn Ile Gln Gln Val Ser Asn
                85                  90                  95

Pro Ser Gly Thr Leu Thr Thr Gly Leu Gly Glu Pro Lys Phe Asn
            100                 105                 110

Val Asp Glu Thr Ala Phe Thr Gly Ala Trp Gly Arg Pro Gln Arg Asp
            115                 120                 125

Gly Pro Ala Leu Arg Ala Thr Ala Leu Ile Thr Tyr Gly Asn Trp Leu
130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Ser Phe Phe Thr Thr Ala
            180                 185                 190

Val Gln His Arg Ala Leu Arg Glu Gly Ala Ala Phe Ala Thr Lys Ile
            195                 200                 205

Gly Gln Thr Ser Ser Val Ser Ser Tyr Thr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
            260                 265                 270

Phe Gln Pro Cys Ser Asp Lys Ala Leu Ser Asn Leu Lys Val Tyr Val
            275                 280                 285

Asp Ser Phe Arg Ser Val Tyr Ser Ile Asn Ser Gly Ile Ala Ser Asn
290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
            340                 345                 350

Ser Leu Pro Phe Phe Gln Gln Phe Ser Ser Val Thr Ala Gly Thr
            355                 360                 365

Tyr Ala Ser Ser Ser Thr Thr Tyr Thr Thr Leu Thr Ser Ala Ile Lys
    370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
            405                 410                 415

Ser Ala Val Asp Leu Thr Trp Ser Tyr Ala Ser Ala Leu Thr Ala Phe
            420                 425                 430
```

```
Glu Ala Arg Asn Asn Thr Gln Phe Ala Gly Trp Gly Ala Val Gly Leu
            435                 440                 445

Thr Val Pro Thr Ser Cys Ser Ser Asn Ser Gly Gly Gly Gly Gly Ser
450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
            485                 490                 495

Asp Asn Ala Leu Leu Ser Ser Ala Asn Tyr Pro Thr Trp Ser Ile
            500                 505                 510

Thr Val Asn Leu Pro Ala Ser Thr Ala Ile Gln Tyr Lys Tyr Ile Arg
            515                 520                 525

Lys Asn Asn Gly Ala Val Thr Trp Glu Ser Asp Pro Asn Asn Ser Ile
            530                 535                 540

Thr Thr Pro Ala Ser Gly Ser Val Thr Glu Asn Asp Thr Trp Arg
545                 550                 555

<210> SEQ ID NO 14
<211> LENGTH: 556
<212> TYPE: PRT
<213> ORGANISM: Trametes cingulata

<400> SEQUENCE: 14

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
            35                  40                  45

Asn Tyr Leu Tyr Thr Trp Thr Arg Asp Ser Ser Leu Val Phe Lys Ala
    50                  55                  60

Leu Ile Asp Gln Phe Thr Thr Gly Glu Asp Thr Ser Leu Arg Thr Leu
65              70                  75                  80

Ile Asp Glu Phe Thr Ser Ala Glu Ala Ile Leu Gln Gln Val Pro Asn
            85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
            115                 120                 125

Gly Pro Ala Leu Arg Ala Thr Ala Ile Ile Thr Tyr Ala Asn Trp Leu
130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
            165                 170                 175

Phe Asp Leu Trp Glu Glu Ile Asn Ser Ser Ser Phe Phe Thr Thr Ala
            180                 185                 190

Val Gln His Arg Ala Leu Arg Glu Gly Ala Thr Phe Ala Asn Arg Ile
            195                 200                 205

Gly Gln Thr Ser Val Val Ser Gly Tyr Thr Thr Gln Ala Asn Asn Leu
            210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
            245                 250                 255
```

```
Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr
            340                 345                 350

Ser Leu Pro Phe Phe Gln Gln Phe Ser Ser Gly Val Thr Val Gly Thr
        355                 360                 365

Tyr Ala Ser Ser Ser Ser Thr Phe Lys Thr Leu Thr Ser Ala Ile Lys
370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Leu Thr Ser Phe
            420                 425                 430

Ala Ala Arg Ser Gly Lys Thr Tyr Ala Ser Trp Gly Ala Ala Gly Leu
            435                 440                 445

Thr Val Pro Thr Thr Cys Ser Gly Gly Ala Gly Thr Val Ala
450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
            485                 490                 495

Leu Ile Leu Ser Ala Ala Asn Tyr Pro Thr Trp Ser Ile Thr Val Asn
                500                 505                 510

Leu Pro Ala Ser Thr Thr Ile Glu Tyr Lys Tyr Ile Arg Lys Phe Asn
        515                 520                 525

Gly Ala Val Thr Trp Glu Ser Asp Pro Asn Asn Ser Ile Thr Thr Pro
530                 535                 540

Ala Ser Gly Thr Phe Thr Gln Asn Asp Thr Trp Arg
545                 550                 555

<210> SEQ ID NO 15
<211> LENGTH: 583
<212> TYPE: PRT
<213> ORGANISM: Artificial
<220> FEATURE:
<223> OTHER INFORMATION: Synthetic construct

<400> SEQUENCE: 15

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60
```

-continued

```
Lys Asn Ser Asp Gly Gly Tyr His Gly Tyr Trp Ala Thr Asp Phe Tyr
 65                  70                  75                  80

Gln Leu Asn Ser Asn Phe Gly Asp Glu Ser Gln Leu Lys Ala Leu Ile
                 85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445

Thr Gly Ser Gly Ser Val Thr Ser Thr Ser Lys Thr Thr Ala Thr Ala
450                 455                 460

Ser Lys Thr Ser Thr Ser Thr Ser Ser Thr Ser Cys Thr Thr Pro Thr
465                 470                 475                 480
```

```
Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 16
<211> LENGTH: 595
<212> TYPE: PRT
<213> ORGANISM: Penicillium oxalicum

<400> SEQUENCE: 16

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270
```

Pro Glu Ala Ala Cys Asp Asp Ala Thr Phe Gln Pro Cys Ser Ala Arg
            275                 280                 285

Ala Leu Ala Asn His Lys Val Tyr Val Asp Ser Phe Arg Ser Ile Tyr
        290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Leu Ser Phe Phe Lys Asp
        355                 360                 365

Phe Asp Ala Thr Val Lys Ile Gly Ser Tyr Ser Arg Asn Ser Lys Thr
        370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
        530                 535                 540

Val Glu Phe Ile Pro Ala Gly Thr Pro Phe Glu Tyr Lys Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595

<210> SEQ ID NO 17
<211> LENGTH: 674
<212> TYPE: PRT
<213> ORGANISM: Myceliophthora sepedonium

<400> SEQUENCE: 17

Leu Tyr Ile Asn Gly Ser Val Thr Ala Pro Cys Asp Ser Pro Ile Tyr
1               5                   10                  15

Cys Gln Gly Glu Leu Leu Lys Ala Val Glu Leu Ala Arg Pro Phe Val
            20                  25                  30

Asp Ser Lys Thr Phe Val Asp Met Pro Thr Ile Lys Pro Val Asp Glu

```
            35                  40                  45
Val Leu Ala Ala Phe Ser Lys Leu Ser Leu Pro Leu Ser Asn Asn Ser
 50                  55                  60

Glu Leu Asn Ala Phe Leu Tyr Glu Asn Phe Ala Gln Ala Gly His Glu
 65                  70                  75                  80

Leu Glu Glu Val Pro Asp Ser Glu Leu Glu Thr Asp Ala Lys Phe Leu
                     85                  90                  95

Asp Lys Leu Glu Asp Arg Thr Ile Lys Glu Phe Val Gly Lys Val Ile
                100                 105                 110

Asp Ile Trp Pro Asp Leu Thr Arg Arg Tyr Ala Gly Pro Ser Asn Cys
                115                 120                 125

Thr Glu Cys Ala Asn Ser Phe Ile Pro Val Asn Arg Thr Phe Val Val
130                 135                 140

Ala Gly Gly Arg Phe Arg Glu Pro Tyr Tyr Trp Asp Ser Tyr Trp Ile
145                 150                 155                 160

Val Glu Gly Leu Leu Arg Thr Gly Gly Ala Phe Thr His Ile Ser Lys
                165                 170                 175

Asn Ile Ile Glu Asn Phe Leu Asp Phe Val Asp Thr Ile Gly Phe Ile
                180                 185                 190

Pro Asn Gly Ala Arg Ile Tyr Tyr Leu Asn Arg Ser Gln Pro Pro Leu
                195                 200                 205

Leu Thr Leu Met Val Lys Ser Tyr Val Asp Tyr Thr Asn Asp Thr Ser
210                 215                 220

Ile Leu Asp Arg Ala Leu Pro Leu Leu Ile Lys Glu His Glu Phe Phe
225                 230                 235                 240

Met Asn Asn Arg Thr Val Ser Ile Thr Gly Ser Asn Gly Lys Glu Tyr
                    245                 250                 255

Thr Leu Asn Arg Tyr His Val Glu Asn Asn Gln Pro Arg Pro Glu Ser
                260                 265                 270

Phe Arg Glu Asp Tyr Ile Thr Ala Asn Asn Gly Ser Tyr Tyr Ala Ser
                275                 280                 285

Ser Gly Ile Ile Tyr Pro Val Lys Thr Pro Leu Asn Glu Thr Glu Lys
                290                 295                 300

Ala Ala Leu Tyr Ser Asn Leu Ala Thr Gly Ala Glu Ser Gly Trp Asp
305                 310                 315                 320

Tyr Thr Ser Arg Trp Leu Gly Val Pro Ser Asp Ala Ala Arg Asp Val
                    325                 330                 335

Tyr Phe Pro Leu Arg Ser Leu Asn Val Arg Asp Ile Val Pro Val Asp
                340                 345                 350

Leu Asn Ser Ile Leu Tyr Gln Asn Glu Val Ile Ile Ala Glu Tyr Leu
                355                 360                 365

Glu Lys Ala Gly Asn Ser Ser Ala Ala Lys Arg Phe Ala Thr Ala Ala
                370                 375                 380

Glu Gln Arg Ser Glu Ala Met Tyr Ser Leu Met Trp Asn Ala Thr His
385                 390                 395                 400

Trp Ser Tyr Phe Asp Tyr Asn Leu Thr Asp Asn Thr Gln His Ile Phe
                    405                 410                 415

Val Pro Ala Asp Glu Asp Thr Ala Pro Gln Asp Arg Ile Glu Ala Pro
                420                 425                 430

Pro Gly Gln Gln Val Phe Phe His Ile Ala Gln Leu Tyr Pro Phe Trp
                435                 440                 445

Thr Gly Ala Ala Pro Ala Ser Leu Lys Ala Asn Pro Leu Ala Val Gln
450                 455                 460
```

```
Gln Ala Tyr Ala Arg Val Ala Arg Met Leu Asp Ile Lys Lys Gly Ala
465                 470                 475                 480

Ile Pro Ala Thr Asn Tyr Arg Thr Gly Gln Gln Trp Asp Gln Pro Asn
                485                 490                 495

Val Trp Pro Pro Leu Gln His Ile Leu Met Lys Gly Leu Leu Asn Thr
            500                 505                 510

Pro Ala Thr Phe Gly Lys Ser Asp Pro Ala Tyr Gln Ser Val Gln Asn
        515                 520                 525

Leu Ala Leu Arg Leu Ala Gln Arg Tyr Leu Asp Ser Thr Phe Cys Thr
        530                 535                 540

Trp Tyr Ala Thr Gly Gly Ser Thr Ser Asp Phe Pro Gln Leu Glu Gly
545                 550                 555                 560

Val Thr Pro Gly Ala Thr Gly Val Met Phe Glu Lys Tyr Ala Asp Asn
            565                 570                 575

Ala Thr Asn Val Ala Gly Gly Gly Glu Tyr Glu Val Val Glu Gly
            580                 585                 590

Phe Gly Trp Thr Asn Gly Val Leu Ile Trp Ala Ala Asp Val Phe Gly
        595                 600                 605

Asn Lys Leu Lys Arg Pro Asp Cys Gly Asn Ile Thr Ala Ala His Thr
        610                 615                 620

His Ser Ser Ala Lys Arg Gly Leu Glu Glu Asn Lys Leu Pro Arg Arg
625                 630                 635                 640

Ala Val Glu Leu Asp Pro Trp Asp Ala Ala Trp Thr Lys Met Phe Gly
            645                 650                 655

Arg Ser Lys Leu Arg Arg Arg Glu Ala Glu Asp Val Arg Lys Arg Trp
            660                 665                 670

Met Ser
```

POLYPEPTIDES HAVING PULLULANASE ACTIVITY SUITABLE FOR USE IN LIQUEFACTION

CROSS-REFERENCE TO RELATED APPLICATIONS

This application is a 35 U.S.C. 371 national application of international application no. PCT/EP2020/057218 filed Mar. 17, 2020, which claims priority or the benefit under 35 U.S.C. 119 of European application no. 19163366.8 filed Mar. 18, 2019, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to use of thermo-stable pullulanase variants in a process for producing fermentation products from starch-containing material and to variant polypeptides having pullulanase activity.

BACKGROUND OF THE INVENTION

Starch usually consists of about 80% amylopectin and 20% amylose. Amylopectin is a branched polysaccharide in which linear chains alpha-1,4 D-glucose residues are joined by alpha-1,6 glucosidic linkages. Amylopectin is partially degraded by alpha-amylase, which hydrolyzes the 1,4-alpha-glucosidic linkages to produce branched and linear oligosaccharides. Prolonged degradation of amylopectin by alpha-amylase results in the formation of so-called alpha-limit dextrins that are not susceptible to further hydrolysis by the alpha-amylase. Branched oligosaccharides can be hydrolyzed into linear oligosaccharides by a debranching enzyme. The remaining branched oligosaccharides can be depolymerized to D-glucose by glucoamylase, which hydrolyzes linear oligosaccharides into D-glucose.

Debranching enzymes which can attack amylopectin are divided into two classes: isoamylases (E.C. 3.2.1.68) and pullulanases (E.C. 3.2.1.41), respectively. Isoamylase hydrolyses alpha-1,6-D-glucosidic branch linkages in amylopectin and beta-limit dextrins and can be distinguished from pullulanases by the inability of isoamylase to attack pullulan, and by their limited action on alpha-limit dextrins.

It is well-known in the art to add isoamylases or pullulanases in starch conversion processes. Pullulanase is a starch debranching enzyme having pullulan 6-glucano-hydrolase activity (EC3.2.1.41) that catalyzes the hydrolyses the α-1,6-glycosidic bonds in pullulan, releasing maltotriose with reducing carbohydrate ends. Usually pullulanase is used in combination with an alpha amylase and/or a glucoamylase.

Pullulanases are known in the art. U.S. Pat. Nos. 6,074,854 and 5,817,498 disclose a pullulanase from *Bacillus deramificans*. WO2009/075682 discloses a pullulanase derived from *Bacillus acidopullulyticus*.

WO 2015/007639 discloses a hybrid pullulanase obtained by combining an N-terminal fragment of a pullulanase from *Bacillus acidopullulyticus* fused to a C-terminal fragment of a pullulanase from *Bacillus deramificans*. Prior art pullulanases derived from *Bacillus* sp. have so far not been sufficiently thermos-stable for use in liquefaction in conventional starch conversion processes.

WO2015/110473 and WO2017/014974 disclose thermo-stabilized pullulanase variants.

It is an object of the present invention to provide pullulanase variants having increased thermo-stability and/or thermo-activity suitable for use in liquefaction of starch containing material.

SUMMARY OF THE INVENTION

The present invention relates to a variant pullulanase, having increased thermo-stability and/or increased thermo-activity compared to a parent pullulanase, comprising a substitution at least at one position selected from a position corresponding to positions 432, 486, 370, 17, 77, 103, 106, 107, 190, 196, 197, 262, 279, 283, 321, 367, 375, 382, 399, 401, 402, 411, 412, 434, 435, 443, 446, 459, 460, 479, 490, 498, 514, 529, 531, 533, 541, 545, 581, 583, 595, 649, 665, 688, 700, 709, 804, 811 of SEQ ID NO: 1, and optionally a deletion of one or more, e.g., all amino acids at positions 821, 822, 823, 824, 825, 826, 827, and 828, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

Further aspect the present invention relates to a process for liquefying starch-containing material at a temperature above the initial gelatinization temperature using an alpha-amylase and a thermo-stable pullulanase of the invention.

Thus, in a second aspect the invention relates to a process for producing a syrup from starch-containing material comprising the steps of:

a) liquefying the starch-containing material at a temperature above the initial gelatinization temperature using an alpha-amylase and a variant pullulanase of the invention;

b) saccharifying using a glucoamylase.

In a third aspect the present invention relates to a process for producing fermentation products from starch-containing material comprising the steps of:

a) liquefying the starch-containing material at a temperature above the initial gelatinization temperature using an alpha-amylase and a variant pullulanase of the invention;

b) saccharifying using a glucoamylase;

c) fermenting using a fermenting organism.

In a fourth aspect the present invention relates to compositions comprising the variant pullulanase of the invention and a stabilizer.

The present invention also relates to polynucleotides encoding the variants; nucleic acid constructs, vectors, and host cells comprising the polynucleotides; and methods of producing the variants.

Furthermore, the present invention relates to use of the variant pullulanase of the invention in liquefaction of starch-containing material.

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to one or more control sequences that provide for its expression. Each control sequence may be native (i.e., from the same gene) or foreign (i.e., from a different gene) to the polynucleotide encoding the polypeptide Fragment: The term "fragment" means a polypeptide having one or more (e.g., several) amino acids absent from the amino and/or carboxyl terminus of a mature polypeptide or domain; wherein the fragment has pullulanas activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Mature polypeptide: The term "mature polypeptide" means a polypeptide in its final form following translation and any post-translational modifications, such as N-terminal processing and C-terminal truncation.

Mature polypeptide coding sequence: The term "mature polypeptide coding sequence" means a polynucleotide that encodes a mature polypeptide having pullulanase activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to the procedure described in the Examples. In the context of the present invention the variant pullulanases have increased thermo-activity and or increased thermo-stability. Pullulanase activity was determined (using the PHADEBAS assay) as relative activity after heat stress/shock for 30 min at two different temperatures in the range from 60-90° C., e.g., 70-87° C., and assayed at a temperature in the range from 60° C.-80° C., e.g., 70° C., depending on the thermo-stability of the variant (thermo-stability), or as relative activity determined at two different temperatures (70-86° C.) (thermoprofile/thermo-activity) as described in the examples. Increased thermo-stability was also measured using the TSA assay for determining melting/denaturing temperature of the variant polypeptides.

Wild-type Pullulanase: The term "wild-type" pullulanase means a pullulanase expressed by a naturally occurring microorganism, such as a bacterium, yeast, or filamentous fungus found in nature.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the-nobrief option) is used as the percent identity and is calculated as follows:

(Identical Deoxyribonucleotides×100)/(Length of
Alignment−Total Number of Gaps in Alignment)

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.]

Subsequence: The term "subsequence" means a polynucleotide having one or more (e.g., several) nucleotides absent from the 5' and/or 3' end of a mature polypeptide coding sequence; wherein the subsequence encodes a fragment having pullulanase activity.

S8A Protease: The term "S8A protease" means an S8 protease belonging to subfamily A. Subtilisins, EC 3.4.21.62, are a subgroup in subfamily S8A.

Variant: The term "variant" means a polypeptide having pullulanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In describing variants, the nomenclature described below is adapted for ease of reference. The accepted IUPAC single letter or three letter amino acid abbreviations are employed.

In the context of the present invention the variant pullulanases has increased thermo-stability and/or increased thermo-activity.

Thermo-stability may be determined (using the PHADEBAS assay) as relative activity after heat stress/shock for 30 min at two different temperatures in the range from 60-90° C., e.g., 70-87° C., and assayed at a temperature in the range from 60° C.-80° C., e.g., 70° C., depending on the thermo-stability of the variant (thermo-stability), or as relative activity determined at two different temperatures (70-86° C.) (thermoprofile/thermo-activity) as described in the examples. Increased thermo-stability may also be measured using the TSA assay for determining melting/denaturing temperature of the variant polypeptides. In one embodiment the pullulanase variants of the invention have an increase in thermo-stability determined as increased melting (denaturing) temperature compared to the parent pullulanase disclosed in SEQ ID NO: 3 using TSA assay of at least 0.3 degrees C., at least 0.4 degrees C., at least 0.5 degrees C., at least 0.6 degrees C., at least 0.8 degrees C., at least 1.0 degrees C., at least 1.2 degrees C., at least 1.5 degrees C., at least 2.0 degrees C., at least 2.5 degrees C., at least 3.0 degrees C., at least 3.5 degrees C., at least 4.0 degrees C., at least 4.5 degrees C., at least 5.0 degrees C.

Increased thermo-stability was measured as described in the examples using the PHADEBAS assay by heat-shock for e.g., 30 min at a temperature in the range from 70–87° C. and then activity was assayed at e.g., 70° C. or 80° C. Thermo-stability was then determined as relative activity of the sample heat-shocked at the higher temperature over the activity of the sample heat-shocked at the lower temperature. E.g., for variant P609 (table 1a of example 2) when heat-shocked at 81.5° C. and at 80° C. the relative activity was 58%, meaning that after incubation at 81.5° C. the activity was 58% compared to the sample incubated at 80° C. Activity was then calculated as relative activity to the parent pullulanase, JPUL604 (SEQ ID NO: 3). The skilled person will know what will be an appropriate temperature to use for heat-shock/stress and for activity assay since this will depend on the thermo-stability of the parent pullulanase and of the resulting variant.

Increased thermo-activity(thermo-profile) was determined as relative activity using the PHADEBAS assay by performing the activity assay at two different temperatures, e.g., in the range 70-86° C., and calculating the % activity at the higher temperature compared to the lower temperature. In some examples thermo-activity was determined by enzymatic reaction with the substrate maltodextrin/pullulan (DE3) at high temperature e.g. 2 hours at 85° C. or 30 min 91° C. Subsequently, the pullulanase digested fraction of maltodextrin was measured by PAHBAH assay at 55° C.

In one embodiment pullulanase variants of the invention have an increase in thermo-activity relative to a parent pullulanase, e.g., the pullulanase disclosed as SEQ ID NO: 3, of at least 5%, at least 10%, at least 20%, at least 25%, at least 30%, at least 35%, at least 40%, at least 50%, at least 60%, at least 70%, at least 80%, at least 90%, at least 100%, after enzymatic reaction of maltodextrin 2 hours at 85° C. or 30 min 91° C., and subsequent determination of digested maltodextrin fraction by PAHBAH assay at 55° C.

Conventions for Designation of Variants

For purposes of the present invention, the mature hybrid pullulanase polypeptide disclosed as SEQ ID NO: 1 is used to determine the corresponding amino acid residue in another pullulanase. The amino acid sequence of another pullulanase is aligned with the mature polypeptide disclosed as SEQ ID NO: 1, and based on the alignment, the amino acid position number corresponding to any amino acid residue in the mature polypeptide disclosed as SEQ ID NO: 1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another pullulanase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), and EMBOSS EMMA employing ClustalW (1.83 or later; Thompson et al., 1994, Nucleic Acids Research 22: 4673-4680), using their respective default parameters.

When the other enzyme has diverged from the polypeptide of SEQ ID NO: 1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The accepted IUPAC single letter or three letter amino acid abbreviations are employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a |
|         | 195b     |
| G       | G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

Throughout the present description in some embodiments the variants of the invention have been described by giving the amino acid present at the specified position in SEQ ID NO: 1 as well as the amino acid present after substitution. This does not mean that the starting amino acid in the specified position cannot be a different one. The starting amino acid in a specific position of course depends on the choice of the parent pullulanase, thus in the present disclosure sometimes the starting amino acid has been denoted X, meaning that this could be any amino acid. The essential feature of the present invention is the resulting amino acid present after the substitution.

DETAILED DESCRIPTION OF THE INVENTION

The present invention relates to variant pullulanases derived from a hybrid parent pullulanase. The hybrid pullulanase, disclosed as SEQ ID NO: 1 herein, was used as the parent pullulanase. The polynucleotide sequence encoding the parent pullulanase is included herein as SEQ ID NO: 2, wherein nucleotides 1-99 encode a signal peptide, and nucleotides 100-2583 encode the mature polypeptide disclosed in SEQ ID NO: 1. In other embodiments the parent pullulanase is selected from the pullulanases disclosed in SEQ ID NO: 3, SEQ ID NO: 4, and SEQ ID NO: 5.

The variants according to the present invention have improved properties compared to the parent. The improved properties are selected from increased thermo-activity (thermo-profile), and/or increased thermo-stability. Pullulanase activity may be determined using any suitable pullulanase assay, such as e.g., by the PHADEBAS assay, or the PAHBAH-pullulan assay described herein in the pullulanase assay section and examples.

Particularly, the present invention relates to a pullulanase variant, having increased thermo-stability and/or increased thermo-activity compared to a parent pullulanase, comprising a substitution at least at one position selected from a position corresponding to positions 432, 486, 370, 17, 77, 103, 106, 107, 190, 196, 197, 262, 279, 283, 321, 367, 375, 382, 399, 401, 402, 411, 412, 434, 435, 443, 446, 459, 460, 479, 490, 498, 514, 529, 531, 533, 541, 545, 581, 583, 595, 649, 665, 688, 700, 709, 804, 811 of SEQ ID NO: 1, and optionally a deletion of one or more, e.g., all amino acids at positions 821, 822, 823, 824, 825, 826, 827, and 828, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

Particularly the substitutions are selected from the group consisting of: K370S, F17Y, D77G, S103K, Q106W, A107D, A190I, V196T,C, T197I, T262V, Q279R, N283F, H321V, D367G,N, S375H, N382T, Q399N, N401D, S402Q, N411L, Y412F, F432V, Q434E, L435A, R443G, I446V, G459E, V460E, H479N, T486A,V, I490L, Q498R, V514A, T529L, S531R, A533I, N541D, A545I, L581F, N583D, Q595R, D649A, V665I, D688A, F700L, P709I, E804S, and G811R.

In one aspect the present invention therefore relates to a pullulanase variant, having increased thermo-stability and/or increased thermo-activity compared to a parent pullulanase, comprising a substitution at a position corresponding to position 370 of SEQ ID NO: 1, wherein the variant pullulanase comprises a serine in position 370 using SEQ ID NO: 1 for numbering, particularly a K370S substitution, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

In another aspect the present invention therefore relates to a pullulanase variant, having increased thermo-stability and/or increased thermo-activity compared to a parent pullulanase, comprising a substitution at a position corresponding to position 432 of SEQ ID NO: 1, wherein the variant pullulanase comprises a valine in position 432 using SEQ ID NO: 1 for numbering, particularly a F432V substitution, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

In another aspect the present invention therefore relates to a pullulanase variant, having increased thermo-stability and/or increased thermo-activity compared to a parent pullulanase, comprising a substitution at a position corresponding to position 486 of SEQ ID NO: 1, wherein the variant pullulanase comprises an alanine or a valine in position 486 using SEQ ID NO: 1 for numbering, particularly a T486A,V substitution, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

The increase in thermo-stability may in one embodiment be determined as relative activity after heat stress for 30 min at two different temperatures selected in the range from 60° C.-90° C., e.g., 70° C.-87° C., and subsequently assayed at 60-80° C., such as 70° C. using PHADEBAS assay. Alternatively, thermo-stability may be determined as increased melting (denaturing) temperature compared to the parent pullulanase using TSA assay.

The increase in thermo-activity (thermo profile) may in one embodiment be determined as relative activity determined at two different temperatures selected from the range of 70-86° C. using PHADEBAS assay.

In a further specific embodiment the variant pullulanase of the invention relates to a pullulanase variant, having increased thermo-stability and/or increased thermo-activity compared to a parent pullulanase, comprising a substitution at least at one position selected from a position corresponding to positions 432, 486, 370, 17, 77, 103, 106, 107, 190, 196, 197, 262, 279, 283, 321, 367, 375, 382, 399, 401, 402, 411, 412, 434, 435, 443, 446, 459, 460, 479, 490, 498, 514, 529, 531, 533, 541, 545, 581, 583, 595, 649, 665, 688, 700, 709, 804, 811 of SEQ ID NO: 1, and optionally a deletion of one or more, e.g., all amino acids at positions 821, 822, 823, 824, 825, 826, 827, and 828, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5, and wherein the variant comprises combinations of substitutions and/or deletions selected from the group consisting of:

Q279R+K370S;
H321E+K370S;
K370S+V821*+S822*+P823*+D824*+H825*+G826*+K827*+K828*;
K370S+Q399N;
K370S+N401D;
K370S+F432V;
V196T+K370S;
V196C+K370S;
T197I+K370S;
K370S+V460E;
K370S+T486A;
K370S+T486V;
K370S+I490L;
K370S+V514A;
K370S+T529L;
K370S+S531R;
K370S+Q595R;
H321E+K370S+F432V;
K370S+F432V+V821*+S822*+P823*+D824*+H825*+G826*+K827*+K828*;
K370S+Q399N+F432V;
K370S+N401D+F432V;
V196T+K370S+F432V;
V196C+K370S+F432V;
T197I+K370S+F432V;
K370S+F432V+G459E;
K370S+F432V+T486A;
K370S+F432V+T486V;
V196T+K370S+F432V+T486A;
T197I+K370S+F432V+T486A;
V196T+T197I+K370S+F432V+T486A;
K370S+Q399N+F432V+T486A;
K370S+N401D+F432V+T486A;
K370S+Q399N+N401D+F432V+T486A;
K370S+S531R+F432V+T486A;
K370S+Q595R+F432V+T486A;
K370S+F432V+T486A+S531R+Q595R;
V196T+T197I+K370S+Q399N+N401D+F432V+T486A;
V196T+T197I+K370S+Q399N+N401D+F432V+T486A+Q595R;
T197I+K370S+N401D+F432V+T486A+S531R+Q595R;
T197I+K370S+N401D+F432V+T486A+S531R+Q595R+V821*+S822*+P823*+D824*+H825*+G826*+K827*+K828*;
T197I+K370S+Q399N+N401D+F432V+T486A+Q595R;
S103K+T197I+K370S+N401D+F432V+T486A+S531R+Q595R;
V196T+T197I+K370S+Q399N+N401D+F432V+T486V+Q595R;
T197I+K370S+N401D+F432V+T486V+S531R+Q595R;
V196T+T197I+K370S+Q399N+N401D+F432V+T486A+S531R+Q595R;
D77G+T197I+K370S+N401D+F432V+T486V+S531R+Q595R;
T197I+K370S+N401D+S402Q+F432V+T486V+S531R+Q595R;
T197I+N283F+K370S+N401D+F432V+T486V+S531R+Q595R;
T197I+N283F+K370S+N401D+S402Q+F432V+T486V+S531R+Q595R;
T197I+N283F+K370S+N401D+F432V+L435A+T486V+S531R+Q595R;
D77G+T197I+N283F+K370S+N401D+S402Q+F432V+T486V+S531R+Q595R;
T197I+N283F+K370S+N401D+S402Q+F432V+L435A+T486V+S531R+Q595R;
D77G+T197I+N283F+K370S+N401D+S402Q+F432V+L435A+T486V+S531R+Q595R;
T197I+N283F+K370S+N401D+S402Q+F432V+L435A+T486V+S531R+Q595R+D649A;
D77G+T197I+N283F+K370S+N401D+S402Q+F432V+L435A+T486V+S531R+Q595R+D649A;
D77G+Q106W+T197I+N283F+K370S+N401D+S402Q+F432V+L435A+T486V+S531R+Q595R;
D77G+A107D+T197I+N283F+K370S+N401D+S402Q+F432V+L435A+T486V+S531R+Q595R;
D77G+V196C+T197I+N283F+K370S+N401D+S402Q+F432V+L435A+T486V+S531R+Q595R;
D77G+T197I+N283F+K370S+N401D+S402Q+F432V+L435A+T486V+S531R+N583D+Q595R;
D77G+T197I+N283F+K370S+N401D+S402Q+F432V+L435A+T486V+S531R+Q595R+V821*+S822*+P823*+D824*+H825*+G826*+K827*+K828*;
D77G+T197I+N283F+K370S+N401D+S402Q+F432V+L435A+T486V+S531R+Q595R+D688A+V821*+S822*+P823*+D824*+H825*+G826*+K827*+K828*;
D77G+T197I+N283F+D367G+K370S+N401D+S402Q+F432V+L435A+T486V+S531R+Q595R+V821*+S822*+P823*+D824*+H825*+G826*+K827*+K828*;
D77G+T197I+N283F+D367N+K370S+N401D+S402Q+F432V+L435A+T486V+S531R+Q595R+V821*+S822*+P823*+D824*+H825*+G826*+K827*+K828*;
D77G+T197I+N283F+K370S+S375H+N401D+S402Q+F432V+L435A+T486V+S531R+Q595R+V821*+S822*+P823*+D824*+H825*+G826*+K827*+K828*;

D77G+T197I+N283F+K370S+N382T+N401D+S402Q+F432V+L435A+T486V+S531R+Q595R+V821*+S822*+P823*+D824*+H825*+G826*+K827*+K828*;

D77G+T197I+N283F+K370S+N401D+S402Q+N411L+F432V+L435A+T486V+S531R+Q595R+V821*+S822*+P823*+D824*+H825*+G826*+K827*+K828*;

D77G+T197I+N283F+K370S+N401D+S402Q+Y412F+F432V+L435A+T486V+S531R+Q595R+V821*+S822*+P823*+D824*+H825*+G826*+K827*+K828*;

D77G+T197I+N283F+K370S+N401D+S402Q+F432V+Q434E+L435A+T486V+S531R+Q595R+V821*+S822*+P823*+D824*+H825*+G826*+K827*+K828*;

D77G+T197I+N283F+K370S+N401D+S402Q+F432V+L435A+R443G+T486V+S531R+Q595R+V821*+S822*+P823*+D824*+H825*+G826*+K827*+K828*;

D77G+T197I+N283F+K370S+N401D+S402Q+F432V+L435A+1446V+T486V+S531R+Q595R+V821*+S822*+P823*+D824*+H825*+G826*+K827*+K828*;

D77G+T197I+N283F+K370S+N401D+S402Q+F432V+L435A+T486V+Q498R+S531R+Q595R+V821*+S822*+P823*+D824*+H825*+G826*+K827*+K828*;

D77G+T197I+N283F+K370S+N401D+S402Q+F432V+L435A+T486V+S531R+A533I+Q595R+V821*+S822*+P823*+D824*+H825*+G826*+K827*+K828*;

D77G+T197I+N283F+K370S+N401D+S402Q+F432V+L435A+T486V+S531R+N541D+Q595R+V821*+S822*+P823*+D824*+H825*+G826*+K827*+K828*;

D77G+T197I+N283F+K370S+N401D+S402Q+F432V+L435A+T486V+S531R+A545I+Q595R+V821*+S822*+P823*+D824*+H825*+G826*+K827*+K828*;

D77G+T197I+N283F+K370S+N401D+S402Q+F432V+L435A+T486V+S531R+L581F+Q595R+V821*+S822*+P823*+D824*+H825*+G826*+K827*+K828*;

D77G+T197I+N283F+K370S+N401D+S402Q+F432V+L435A+H479N+T486V+S531R+Q595R+D688A+V821*+S822*+P823*+D824*+H825*+G826*+K827*+K828*;

D77G+T197I+N283F+D367N+K370S+N401D+S402Q+F432V+L435A+T486V+S531R+Q595R+D688A+V821*+S822*+P823*+D824*+H825*+G826*+K827*+K828*;

D77G+T197I+N283F+K370S+S375H+N401D+S402Q+F432V+L435A+T486V+S531R+Q595R+D688A+V821*+S822*+P823*+D824*+H825*+G826*+K827*+K828*;

D77G+T197I+N283F+K370S+N401D+S402Q+Y412F+F432V+L435A+T486V+S531R+Q595R+D688A+V821*+S822*+P823*+D824*+H825*+G826*+K827*+K828*;

D77G+T197I+N283F+K370S+N401D+S402Q+F432V+L435A+T486V+S531R+A533I+Q595R+D688A+V821*+S822*+P823*+D824*+H825*+G826*+K827*+K828*;

D77G+T197I+N283F+K370S+N401D+S402Q+F432V+L435A+T486V+S531R+L581F+Q595R+D688A+V821*+S822*+P823*+D824*+H825*+G826*+K827*+K828*;

D77G T197I N283F D367N K370S S375H N401D S402Q F432V L435A T486V S531R Q595R D688A V821*S822*P823*D824*H825*G826*K827*K828*;

D77G T197I N283F D367N K370S N401D S402Q Y412F F432V L435A T486V S531R Q595R D688A V821*S822*P823*D824*H825*G826*K827*K828*;

D77G T197I N283F D367N K370S N401D S402Q F432V L435A T486V S531R A533I Q595R D688A V821*S822*P823*D824*H825*G826*K827*K828*;

D77G T197I N283F D367N K370S N401D S402Q F432V L435A T486V S531R L581F Q595R D688A V821*S822*P823*D824*H825*G826*K827*K828*;

D77G T197I N283F K370S N401D S402Q F432V L435A T486V S531R Q595R V665I V821*S822*P823*D824*H825*G826*K827*K828*;

D77G T197I N283F K370S N401 D S402Q F432V L435A T486V S531R Q595R F700L V821*S822*P823*D824*H825*G826*K827*K828*;

D77G T197I N283F K370S N401 D S402Q F432V L435A T486V S531R Q595R P709I V821*S822*P823*D824*H825*G826*K827*K828*;

D77G T197I N283F D367N K370S S375H N401 D S402Q Y412F F432V L435A T486V S531R Q595R D688A V821*S822*P823*D824*H825*G826*K827*K828*;

D77G T197I N283F D367N K370S S375H N401D S402Q F432V L435A T486V S531R A533I Q595R D688A V821*S822*P823*D824*H825*G826*K827*K828*;

D77G T197I N283F D367N K370S S375H N401 D S402Q Y412F F432V L435A T486V S531R A533I L581F Q595R D688A V821*S822*P823*D824*H825*G826*K827*K828*;

D77G T197I N283F H321V D367N K370S S375H N401 D S402Q Y412F F432V Q434E L435A T486V S531R A533I L581F Q595R D688A V821*S822*P823*D824*H825*G826*K827*K828*;

D77G T197I N283F H321V D367N K370S S375H N401 D S402Q Y412F F432V L435A T486V Q498R S531R A533I L581F Q595R D688A V821*S822*P823*D824*H825*G826*K827*K828*;

D77G T197I N283F H321V D367N K370S S375H N401 D S402Q Y412F F432V L435A T486V S531R A533I L581F Q595R D688A F700L V821*S822*P823*D824*H825*G826*K827*K828*;

D77G T197I N283F H321V D367N K370S S375H N401 D S402Q Y412F F432V Q434E L435A T486V Q498R S531R A533I L581F Q595R D688A F700L V821*S822*P823*D824*H825*G826*K827*K828*;

F17Y D77G T197I N283F K370S N401D S402Q F432V L435A T486V S531R Q595R V821*S822*P823*D824*H825*G826*K827*K828*;

D77G T197I N283F K370S N401D S402Q F432V L435A T486V S531R Q595R E804S V821*S822*P823*D824*H825*G826*K827*K828*;

D77G T197I N283F K370S N401D S402Q F432V L435A T486V S531R Q595R G811R V821*S822*P823*D824*H825*G826*K827*K828*;

D77G T197I N283F H321V K370S S375H N401 D S402Q Y412F F432V Q434E L435A H479N T486V Q498R S531R A533I L581F Q595R D688A F700L V821*S822*P823*D824*H825*G826*K827*K828*;

D77G A190I T197I N283F K370S S375H N401 D S402Q Y412F F432V Q434E L435A H479N T486V Q498R S531R A533I L581F Q595R D688A F700L V821*S822*P823*D824*H825*G826*K827*K828*;

D77G T197I T262V N283F K370S S375H N401D S402Q Y412F F432V Q434E L435A H479N T486V Q498R S531R A533I L581F Q595R D688A F700L V821*S822*P823*D824*H825*G826*K827*K828*; and D77G A190I T197I N283F H321V D367N K370S S375H N401D S402Q Y412F F432V Q434E L435A T486V Q498R S531R A533I L581F Q595R D688A F700L V821*S822*P823*D824*H825*G826*K827*K828*.

The specific variants above may further comprise the substitutions N222P+Q252A+Q256R+N368G+N393A+Q431E+N610R+G624S+T631S+S632C, and optionally L432F. Particularly, the specific variants above may further comprise the substitutions N222P+Q252A+Q256R+N368G+N393A+Q431E+N610R+G624S+T631S+S632C+N20G+Y28K+H80Y+Q187R+E310A+D311K+Q387L+Q459G+D586S+E699R+S798R, and optionally L432F. More particularly, the variant pullulanases may further comprise the deletions P30*+V31*+N32*, and optionally Q29G.

Even more particularly, the specific variants above may further comprise the substitutions N222P+Q252A+Q256R+N368G+N393A+Q431E++N610R+G624S+T631S+S632C+N20G+Y28K+H80Y+Q187R+E310A+D311K+Q387L+Q459G+D586S+E699R+S798R+Q29G+P30*+V31*+N32*+D57N+D58P+A195G+N202K+A345P+F456W+E560R, and optionally one, two three, four, five or six of L432F, N197T, M402S, N479H, I460V, I514V. Most preferably the variants comprise the substitutions X370S+X432V, particularly K370S+L,F432V, and optionally X492A,S.

The pullulanase variants according to the invention have improved properties compared to the parent pullulanase. In particular, increased thermo-stability and/or increased thermo-activity. In a particular embodiment, the variant pullulanases have an increase in thermo-stability relative to a parent pullulanase, such as the parent disclosed in SEQ ID NO: 3 of at least 5%, at least 10%, at least 20%, at least 25%, at least 30%, at least 35%, at least 40%, at least 50%, at least 60%, at least 70%, at least 80%, at least 90%, or at least 100%, after enzymatic reaction of a maltodextrin substrate 2 hours at 85° C. or 30 min 91° C., and subsequent determination of digested maltodextrin fraction by PAHBAH assay at 55° C. Alternatively, the variant pullulanases have an increase in thermo-stability relative to a parent pullulanase, such as the parent disclosed in SEQ ID NO: 3, determined as increased melting (denaturing) temperature compared to the parent pullulanase disclosed in SEQ ID NO: 3 using TSA assay, of at least 0.3 degrees C., at least 0.4 degrees C., at least 0.5 degrees C., at least 0.6 degrees C., at least 0.8 degrees C., at least 1.0 degrees C., at least 1.2 degrees C., at least 1.5 degrees C., at least 2.0 degrees C., at least 2.5 degrees C., at least 3.0 degrees C., at least 3.5 degrees C., at least 4.0 degrees C., at least 4.5 degrees C., at least 5.0 degrees C.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIII/A gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIII/A gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In yeast, the ADH2 system or GAL1 system may be used.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In,

*Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art. For example, an enzyme assay may be used to determine the activity of the variant. See the Assay section for suitable pullulanase activity assays.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* Janson and Ryden, editors, VCH Publishers, New York, 1989) to obtain substantially pure variants.

In an alternative aspect, the variant is not recovered, but rather a host cell of the present invention expressing the variant is used as a source of the variant. In a particular embodiment, the pullulanase variants of the invention are produced in a yeast host cell which is also used as a fermenting organism in the processes of the invention, e.g., in SSF. Particularly, the yeast is a *Saccharomyces cerevisiae.*

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a pullulanase variant of the invention and a suitable stabilizer.

The compositions may comprise the pullulanase variant as the major enzymatic component, e.g., a mono-component composition. Alternatively, the compositions may comprise multiple enzymatic activities, such as one or more (e.g., several) enzymes selected from the group consisting of alpha-amylase, glucoamylase, beta-amylase, protease.

The compositions may be prepared in accordance with methods known in the art and may be in the form of a liquid or a dry composition. The compositions may be stabilized in accordance with methods known in the art.

Examples are given below of preferred uses of the compositions of the present invention. In a particular embodiment the composition further comprises an alpha-amylase.

The alpha-amylase is preferably a bacterial acid stable alpha-amylase. Particularly the alpha-amylase is from an *Exiguobacterium* sp. or a *Bacillus* sp. such as e.g., *Bacillus stearothermophilus* or *Bacillus licheniformis*.

In an embodiment the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 6 herein.

In an embodiment the *Bacillus stearothermophilus* alpha-amylase has a double deletion of two amino acids in the region from position 179 to 182, more particularly a double deletion at positions I181+G182, R179+G180, G180+I181, R179+I181, or G180+G182, preferably I181+G182, and optionally a N193F substitution, (using SEQ ID NO: 6 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase is selected from the group of *Bacillus stearothermophilus* alpha-amylase variants with the following mutations in addition to a double deletion in the region from position 179 to 182, particularly I181*+G182*and optionally N193F.

In an embodiment the alpha-amylase is selected from the group of *Bacillus stearothermophilus* alpha-amylase variants with the following mutations:

I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V;
I181*+G182*+N193F+V59A Q89R+E129V+K177L+R179S+Q254S+M284V; and
I181*+G182*+N193F+E129V+K177L+R179E+K220P+N224L+S242Q+Q254S (using SEQ ID NO: 6 for numbering).

In an embodiment the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 6.

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 6 herein, or variants thereof, are truncated in the C-terminal preferably to have around 490 amino acids, such as from 482-493 amino acids. Preferably the *Bacillus stearothermophilus* variant alpha-amylase is truncated, preferably after position 484 of SEQ ID NO: 6, particularly after position 485, particularly after position 486, particularly after position 487, particularly after position 488, particularly after position 489, particularly after position 490, particularly after position 491, particularly after position 492, more particularly after position 493.

Protease Present and/or Added During Liquefaction

In a preferred embodiment the enzyme composition of the invention, further comprises a protease.

According to the invention a thermostable protease may optionally be present and/or added during liquefaction together with a variant pullulanase of the invention and an alpha-amylase, such as a thermostable alpha-amylase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In one embodiment the protease is a serine protease or a metallo-protease, such as an S8 serine protease.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay described in the "Materials & Methods" section.

There are no limitations on the origin of the protease used in a process of the invention as long as it fulfills the thermostability properties defined below.

The protease may be a variant of, e.g., a wild-type protease as long as the protease has the thermostability properties defined herein. In a preferred embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 7 herein with the following mutations:

D79L+S87P+A112P+D142L;
D79L+S87P+D142L; or
A27K+D79L+Y82F+S87G+D104P+A112P+A126V+
D142L, and wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 7 herein.

The thermostable protease may also be derived from any bacterium as long as the protease has the thermo-stability properties defined according to the description.

In an embodiment the thermostable protease is derived from a strain of the bacterium *Pyrococcus*, such as a strain of *Pyrococcus furiosus* (pfu protease).

In an embodiment the protease is the one shown as SEQ ID NO: 1 in U.S. Pat. No. 6,358,726-B1 (Takara Shuzo Company) or SEQ ID NO: 8 herein.

In another embodiment the thermostable protease is one disclosed in SEQ ID NO: 8 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 8 herein. The *Pyroccus furiosus* protease can be purchased from Takara Bio, Japan.

In another embodiment, the protease is selected from a *Palaeococcus* sp. S8 protease, particularly a *Palaeococcus ferrophilus* S8 protease shown as SEQ ID NO: 9 or a protease having at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 9.

In an embodiment the composition of the invention comprises:
i) a *Bacillus stearothermophilus* alpha-amylase, or a variant thereof;
ii) a variant pullulanase of the invention;
iii) optionally a protease; and
wherein the ratio between alpha-amylase and protease is in the range from 1:1 and 1:50 (micro gram alpha-amylase: micro gram protease).

In an embodiment the ratio between alpha-amylase and protease is in the range between 1:3 and 1:40, such as around 1:4 (micro gram alpha-amylase:micro gram protease).

In an embodiment the ratio between alpha-amylase and pullulanase is between 1:1 and 1:10, such as around 1:2.5 or 1:5 (micro gram alpha-amylase:micro gram pullulanase).

The pullulanase may according to the invention be added in an effective amount which include the preferred amount of about 2-100 micro gram enzyme protein per gram DS, preferably 5-50 micro gram enzyme protein per gram DS. Pullulanase activity may be determined as NPUN. An Assay for determination of NPUN is described in the assay section.

Carbohydrate-Source Generating Enzyme Present and/or Added During Liquefaction

According to the invention a carbohydrate-source generating enzyme, preferably a thermostable glucoamylase, is present and/or added during liquefaction together with a thermostable alpha-amylase and optionally a thermostable protease. As mentioned above a pullulanase may also be present and/or added during liquefaction step i).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is a thermostable glucoamylase. The carbohydrate-source generating enzyme, in particular thermostable glucoamylase, may be added together with or separately from the thermostable alpha-amylase and optionally the thermostable protease.

In an embodiment the carbohydrate-source generating enzyme, preferably a thermostable glucoamylase, has a Relative Activity heat stability at 85° C. of at least 20%, at least 30%, preferably at least 35%. In an embodiment the carbohydrate-generating enzyme is a glucoamylase having a relative activity at pH 4.5 of at least 80%, preferably at least 85%, preferably at least 90%, preferably at least 95%.

In a specific embodiment the carbohydrate-source generating enzyme is a thermostable glucoamylase, preferably of fungal origin, preferably a filamentous fungi, such as from a strain of the genus *Penicillium*, especially a strain of *Penicillium oxalicum* disclosed as SEQ ID NO: 2 in WO 2011/127802 and shown in SEQ ID NO: 16 herein.

In a preferred embodiment the carbohydrate-source generating enzyme is a variant of the *Penicillium oxalicum* glucoamylase disclosed as SEQ ID NO: 2 in WO 2011/127802 and shown in SEQ ID NOS: 16, having a K79V substitution. In another preferred embodiment the *Penicillium oxalicum* glucoamylase variant has a K79V substitution (using SEQ ID NO: 16 for numbering), and further comprises one of the following mutations:

P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T, and wherein, the glucoamylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 16.

The carbohydrate-source generating enzyme may, in one embodiment, be added in amounts from 0.1-100 micrograms EP/g, such as 0.5-50 micrograms EP/g, such as 1-25 micrograms EP/g, such as 2-12 micrograms EP/g DS.

Processes of the Invention

The present invention relates to processes for producing fermentation products from starch-containing material. In particular the product is an alcohol, more particularly ethanol.

The inventors have found that an increased ethanol yield can be obtained when a pullulanase variant according to the invention, having increased thermo-activity and/or increased thermo-activity, is present or added during liquefaction together with at least an alpha-amylase.

Process of Producing a Fermentation Product of the Invention

In a particular aspect the invention relates to a process for producing a syrup from starch-containing material comprising the steps of:
a) liquefying the starch-containing material at a temperature above the initial gelatinization temperature using an alpha-amylase and a variant pullulanase of the invention;
b) saccharifying using a glucoamylase.

In another particular aspect the invention relates to processes for producing fermentation products from starch-containing material comprising the steps of:
a) liquefying the starch-containing material at a temperature above the initial gelatinization temperature using:
an alpha-amylase and a variant pullulanase of the invention;
b) saccharifying using a glucoamylase;
c) fermenting using a fermenting organism.

In a preferred embodiment the fermentation product is recovered after fermentation, such as by distillation. In an embodiment the fermentation product is an alcohol, preferably ethanol, especially fuel ethanol, potable ethanol and/or industrial ethanol.

Alpha-Amylases Present and/or Added in Liquefaction

The alpha-amylase added during liquefaction step a) in a process of the invention may be any alpha-amylase. Preferred are bacterial alpha-amylases, which typically are stable at a temperature used in liquefaction.

In an embodiment the alpha-amylase is from a strain of the genus *Exiguobacterium* or *Bacillus*.

In a preferred embodiment the alpha-amylase is from a strain of *Bacillus stearothermophilus*, such as the sequence shown in SEQ ID NO: 3 in WO99/019467 or in SEQ ID NO: 6 herein. In an embodiment the alpha-amylase is the *Bacillus stearothermophilus* alpha-amylase shown in SEQ ID NO: 6 herein, such as one having at least 80%, such as at least 85%, such as at least 90%, such as at least 95%, such as at least 96%, such as at least 97%, such as at least 98%, such as at least 99% identity to SEQ ID NO: 6 herein.

In an embodiment the *Bacillus stearothermophilus* alpha-amylase or variant thereof is truncated, preferably at the C-terminal, preferably truncated to have around 491 amino acids, such as from 480-495 amino acids.

In an embodiment the *Bacillus stearothermophilus* alpha-amylase has a double deletion of two amino acids in the region from position 179 to 182, more particularly a double deletion at positions I181+G182, R179+G180, G180+I181, R179+I181, or G180+G182, preferably I181+G182, and optionally a N193F substitution, (using SEQ ID NO: 6 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase is selected from the group of *Bacillus stearothermophilus* alpha-amylase variants with the following mutations in addition to a double deletion in the region from position 179 to 182, particularly I181*+G182*, and optionally N193F.

In a preferred embodiment the alpha-amylase is selected from the group of *Bacillus stearothermophilus* alpha-amylase variants:
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 6 for numbering).

According to the invention the alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 6 herein.

The alpha-amylase may according to the invention be present and/or added in a concentration of 0.1-100 micro gram per gram DS, such as 0.5-50 micro gram per gram DS, such as 1-25 micro gram per gram DS, such as 1-10 micro gram per gram DS, such as 2-5 micro gram per gram DS.

In an embodiment the ratio between alpha-amylase and pullulanase is between 1:1 and 1:10, such as around 1:2.5 or 1:5 (micro gram alpha-amylase:micro gram pullulanase).

The pullulanase may according to the invention be added in an effective amount which include the preferred amount of about 2-100 micro gram enzyme protein per gram DS, preferably 5-50 micro gram enzyme protein per gram DS. Pullulanase activity may be determined as NPUN. An Assay for determination of NPUN is described in the assay section.

Protease Present and/or Added During Liquefaction

In a preferred embodiment the processes of the invention, further comprises adding a protease in liquefaction.

According to the invention a thermostable protease may optionally be present and/or added during liquefaction together with a variant pullulanase of the invention and an alpha-amylase, such as a thermostable alpha-amylase.

For more details on suitable proteases see the composition section above.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 7 herein with the following mutations:

D79L+S87P+A112P+D142L;
D79L+S87P+D142L; or
A27K+D79L+Y82F+S87G+D104P+A112P+A126V+
D142L, and wherein, the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 7 herein.

The thermostable protease may also be derived from any bacterium as long as the protease has the thermo-stability properties defined according to the description.

In an embodiment the thermostable protease is derived from a strain of the bacterium *Pyrococcus*, such as a strain of *Pyrococcus furiosus* (pfu protease).

In an embodiment the protease is the one shown as SEQ ID NO: 1 in U.S. Pat. No. 6,358,726-B1 (Takara Shuzo Company) or SEQ ID NO: 8 herein.

In another embodiment the thermostable protease is one disclosed in SEQ ID NO: 8 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 8 herein. The *Pyroccus furiosus* protease can be purchased from Takara Bio, Japan.

Glucoamylase Present and/or Added in Saccharification and/or Fermentation

A glucoamylase is present and/or added in saccharification and/or fermentation, preferably simultaneous saccharification and fermentation (SSF), in a process of the invention (i.e., oil recovery process and fermentation product production process).

In an embodiment the glucoamylase present and/or added in saccharification and/or fermentation is of fungal origin, preferably from a stain of *Aspergillus*, preferably *A. niger*, *A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, or a strain of *Gloeophyllum*, such as *G. sepiarium* or *G. trabeum*, or a strain of the *Nigrofomes*.

In an embodiment the glucoamylase is derived from *Talaromyces*, such as a strain of *Talaromyces emersonii*, such as the one shown in SEQ ID NO: 10 herein, In an embodiment the glucoamylase is selected from the group consisting of:
(i) a glucoamylase comprising the polypeptide of SEQ ID NO: 10 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 10 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576 or SEQ ID NO: 11 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 12 herein.

In a preferred embodiment the glucoamylase is derived from *Gloeophyllum sepiarium*, such as the one shown in SEQ ID NO: 12 herein. In an embodiment the glucoamylase is selected from the group consisting of:
(i) a glucoamylase comprising the polypeptide of SEQ ID NO: 12 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12 herein.

In another embodiment the glucoamylase is derived from *Gloeophyllum trabeum* such as the one shown in SEQ ID NO: 13 herein. In an embodiment the glucoamylase is selected from the group consisting of:
(i) a glucoamylase comprising the polypeptide of SEQ ID NO: 13 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 13 herein.

In an embodiment the glucoamylase is derived from a strain of the genus *Trametes*, in particular a strain of *Trametes cingulata* disclosed in WO 2006/069289, and herein as SEQ ID NO: 14.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont.); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with an alpha-amylase. Examples of suitable alpha-amylase are described below.

Alpha-Amylase Present and/or Added in Saccharification and/or Fermentation

In an embodiment an alpha-amylase is present and/or added in saccharification and/or fermentation in a process of the invention. In a preferred embodiment the alpha-amylase is of fungal or bacterial origin. In a preferred embodiment the alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 15 herein, or a variant thereof.

In an embodiment the alpha-amylase present and/or added in saccharification and/or fermentation is selected from the group consisting of:
  (i) an alpha-amylase comprising the polypeptide of SEQ ID NO: 15 herein;
  (ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15 herein.

In a preferred embodiment the alpha-amylase is a variant of the alpha-amylase shown in SEQ ID NO: 15 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 15 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 15 herein, preferably having one or more of the following substitutions: G128D, D143N, preferably G128D+D143N (using SEQ ID NO: 15 for numbering).

In an embodiment the alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 15 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Further Aspects of Processes of the Invention

Prior to liquefaction step a), processes of the invention, may comprise the steps of:
  i) reducing the particle size of the starch-containing material, preferably by dry milling;
  ii) forming a slurry comprising the starch-containing material and water.

In an embodiment at least 50%, preferably at least 70%, more preferably at least 80%, especially at least 90% of the starch-containing material fit through a sieve with #6 screen.

In an embodiment the pH during liquefaction is between above 4.5-6.5, such as 4.5-5.0, such as around 4.8, or a pH between 5.0-6.2, such as 5.0-6.0, such as between 5.0-5.5, such as around 5.2, such as around 5.4, such as around 5.6, such as around 5.8.

In an embodiment the temperature during liquefaction is above the initial gelatinization temperature, preferably in the range from 70-100° C., such as between 75-95° C., such as between 75-90° C., preferably between 80-90° C., especially around 85° C.

In an embodiment a jet-cooking step is carried out before liquefaction in step a). In an embodiment the jet-cooking is carried out at a temperature between 110-145° C., preferably 120-140° C., such as 125-135° C., preferably around 1300C for about 1-15 minutes, preferably for about 3-10 minutes, especially around about 5 minutes.

In a preferred embodiment saccharification and fermentation is carried out sequentially or simultaneously.

In an embodiment saccharification is carried out at a temperature from 20-75° C., preferably from 40-70° C., such as around 60° C., and at a pH between 4 and 5.

In an embodiment fermentation or simultaneous saccharification and fermentation (SSF) is carried out carried out at a temperature from 25° C. to 400C, such as from 28° C. to 35° C., such as from 30° C. to 34° C., preferably around about 32° C. In an embodiment fermentation is ongoing for 6 to 120 hours, in particular 24 to 96 hours.

In a preferred embodiment the fermentation product is recovered after fermentation, such as by distillation.

In an embodiment the fermentation product is an alcohol, preferably ethanol, especially fuel ethanol, potable ethanol and/or industrial ethanol.

In an embodiment the starch-containing starting material is whole grains. In an embodiment the starch-containing material is selected from the group of corn, wheat, barley, rye, milo, sago, cassava, manioc, tapioca, sorghum, rice, and potatoes.

In an embodiment the fermenting organism is yeast, preferably a strain of *Saccharomyces*, especially a strain of *Saccharomyces cerevisae*.

In an embodiment the temperature in step (a) is above the initial gelatinization temperature, such as at a temperature between 80-90° C., such as around 85° C.

In an embodiment a process of the invention further comprises a pre-saccharification step, before saccharification step b), carried out for 40-90 minutes at a temperature between 30-65° C. In an embodiment saccharification is carried out at a temperature from 20-75° C., preferably from 40-70° C., such as around 60° C., and at a pH between 4 and 5. In an embodiment fermentation step c) or simultaneous saccharification and fermentation (SSF) (i.e., steps b) and c)) are carried out carried out at a temperature from 25° C. to 40° C., such as from 28° C. to 35° C., such as from 30° C. to 34° C., preferably around about 32° C. In an embodiment the fermentation step c) or simultaneous saccharification and fermentation (SSF) (i.e., steps b) and c)) are ongoing for 6 to 120 hours, in particular 24 to 96 hours.

In an embodiment the fermentation product is recovered by distillation.

Fermentation Medium

The environment in which fermentation is carried out is often referred to as the "fermentation media" or "fermentation medium". The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae*.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from 105 to $10^{12}$, preferably from $10^7$ to $10^{10}$, especially about $5 \times 10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery of Fermentation Products

Subsequent to fermentation, or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art.

The invention is further summarized in the following numbered paragraphs:

1. A variant pullulanase, having increased thermo-stability and/or increased thermo-activity compared to a parent pullulanase, comprising a substitution at least at one position selected from a position corresponding to positions 432, 486, 370, 17, 77, 103, 106, 107, 190, 196, 197, 262, 279, 283, 321, 367, 375, 382, 399, 401, 402, 411, 412, 434, 435, 443, 446, 459, 460, 479, 490, 498, 514, 529, 531, 533, 541, 545, 581, 583, 595, 649, 665, 688, 700, 709, 804, and 811 of SEQ ID NO: 1, and optionally a deletion of one or more, e.g., all amino acids at positions 821, 822, 823, 824, 825, 826, 827, and 828, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

2. The variant pullulanase of paragraph 1, comprising a substitution at a position corresponding to position 432 of SEQ ID NO: 1, wherein the variant pullulanase comprises valine in position 432 using SEQ ID NO: 1 for numbering, particularly a F432V substitution, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

3. The variant pullulanase of paragraph 1, comprising a substitution at a position corresponding to position 486 of SEQ ID NO: 1, wherein the variant pullulanase comprises alanine or valine in position 486 using SEQ ID NO: 1 for numbering, particularly a T486A,V substitution, wherein the variant has pullulanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

4. The variant pullulanase of paragraph 1, comprising a substitution at a position corresponding to position 370 of SEQ ID NO: 1, wherein the variant pullulanase comprises serine in position 370 using SEQ ID NO: 1 for numbering, particularly a K370S substitution, wherein the variant has pullanase activity, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 3, SEQ ID NO: 4, SEQ ID NO: 5.

5. The variant pullulanase of any of the preceding paragraphs, wherein the substitutions are selected from the group consisting of: K370S, F17Y, D77G, S103K, Q106W, A107D, A190I, V196T,C, T197I, T262V, Q279R, N283F, H321V, D367G,N, S375H, N382T, Q399N, N401D, S402Q, N411L, Y412F, F432V, Q434E, L435A, R443G, I446V, G459E, V460E, H479N, T486A,V, I490L, Q498R, V514A, T529L, S531R, A533I, N541D, A545I, L581F, N583D, Q595R, D649A, V665I, D688A, F700L, P709I, E804S, and G811R.

6. The variant pullulanase according to any of paragraphs 1-5, wherein thermo-stability is determined as relative activity after heat stress for 30 min at two different temperatures, e.g., selected in the range from 60° C.-90° C., e.g., 70° C.-87° C., and subsequently assayed at 60-80° C., e.g., 70° C., using PHADEBAS assay.

7. The variant pullulanase according to any of paragraphs 1-5, wherein thermo-stability is determined as increased melting (denaturing) temperature compared to the parent pullulanase using TSA assay.

8. The variant pullulanase according to any of paragraphs 1-5, wherein thermo-activity is determined as relative activity determined at two different temperatures selected from the range of 70-86° C. using PHADEBAS assay.

9. The variant pullulanase according to any of the preceding paragraphs, wherein the variant comprises combinations of substitutions and/or deletions selected from the group consisting of:
Q279R+K370S;
H321E+K370S;
K370S+V821*+S822*+P823*+D824*+H825*+G826*+K827*+K828*;
K370S+Q399N;
K370S+N401D;
K370S+F432V;
V196T+K370S;
V196C+K370S;
T197I+K370S;
K370S+V460E;
K370S+T486A;
K370S+T486V;
K370S+I490L;
K370S+V514A;
K370S+T529L;
K370S+S531R;
K370S+Q595R;
H321E+K370S+F432V;
K370S+F432V+V821*+S822*+P823*+D824*+H825*+G826*+K827*+K828*;
K370S+Q399N+F432V;
K370S+N401D+F432V;
V196T+K370S+F432V;
V196C+K370S+F432V;
T197I+K370S+F432V;
K370S+F432V+G459E;
K370S+F432V+T486A;
K370S+F432V+T486V;
V196T+K370S+F432V+T486A;
T197I+K370S+F432V+T486A;
V196T+T197I+K370S+F432V+T486A;
K370S+Q399N+F432V+T486A;
K370S+N401 D+F432V+T486A;
K370S+Q399N+N401 D+F432V+T486A;
K370S+S531R+F432V+T486A;
K370S+Q595R+F432V+T486A;
K370S+F432V+T486A+S531R+Q595R;
V196T+T197I+K370S+Q399N+N401D+F432V+T486A; V196T+T197I+K370S+Q399N+N401D+F432V+T486A+Q595R;
T197I+K370S+N401 D+F432V+T486A+S531R+Q595R;
T197I+K370S+N401D+F432V+T486A+S531R+Q595R+V821*+S822*+P823*+D824*+H825*+G826*+K827*+K828*;
T197I+K370S+Q399N+N401D+F432V+T486A+Q595R;
S103K+T197I+K370S+N401D+F432V+T486A+S531R+Q595R;
V196T+T197I+K370S+Q399N+N401D+F432V+T486V+Q595R;
T197I+K370S+N401 D+F432V+T486V+S531R+Q595R;
V196T+T197I+K370S+Q399N+N401D+F432V+T486A+S531R+Q595R;
D77G+T197I+K370S+N401D+F432V+T486V+S531R+Q595R;
T197I+K370S+N401D+S402Q+F432V+T486V+S531R+Q595R;
T197I+N283F+K370S+N401D+F432V+T486V+S531R+Q595R;
T197I+N283F+K370S+N401D+S402Q+F432V+T486V+S531R+Q595R;
T197I+N283F+K370S+N401D+F432V+L435A+T486V+S531R+Q595R;
D77G+T197I+N283F+K370S+N401 D+S402Q+F432V+T486V+S531R+Q595R;
T197I+N283F+K370S+N401D+S402Q+F432V+L435A+T486V+S531R+Q595R;
D77G+T197I+N283F+K370S+N401D+S402Q+F432V+L435A+T486V+S531R+Q595R;
T197I+N283F+K370S+N401D+S402Q+F432V+L435A+T486V+S531R+Q595R+D649A; D77G+T197I+N283F+K370S+N401 D+S402Q+F432V+L435A+T486V+S531R+Q595R+D649A; D77G+Q106W+T197I+N283F+K370S+N401 D+S402Q+F432V+L435A+T486V+S531R+Q595R;
D77G+A107D+T197I+N283F+K370S+N401D+S402Q+F432V+L435A+T486V+S531R+Q595R;
D77G+V196C+T197I+N283F+K370S+N401D+S402Q+F432V+L435A+T486V+S531R+Q595R;
D77G+T197I+N283F+K370S+N401 D+S402Q+F432V+L435A+T486V+S531R+N583D+Q595R;
D77G+T197I+N283F+K370S+N401 D+S402Q+F432V+L435A+T486V+S531R+Q595R+V821*+S822*+P823*+D824*+H825*+G826*+K827*+K828*;
D77G+T197I+N283F+K370S+N401 D+S402Q+F432V+L435A+T486V+S531R+Q595R+D688A+V821*+S822*+P823*+D824*+H825*+G826*+K827*+K828*;
D77G+T197I+N283F+D367G+K370S+N401D+S402Q+F432V+L435A+T486V+S531R+Q595R+V821*+S822*+P823*+D824*+H825*+G826*+K827*+K828*;

D77G+T197I+N283F+D367N+K370S+N401D+S402Q+
F432V+L435A+T486V+S531R+Q595R+V821*+
S822*+P823*+D824*+H825*+G826*+K827*+
K828*;
D77G+T197I+N283F+K370S+S375H+N401 D+S402Q+
F432V+L435A+T486V+S531R+Q595R+V821*+
S822*+P823*+D824*+H825*+G826*+K827*+
K828*;
D77G+T197I+N283F+K370S+N382T+N401D+S402Q+
F432V+L435A+T486V+S531R+Q595R+V821*+
S822*+P823*+D824*+H825*+G826*+K827*+
K828*;
D77G+T197I+N283F+K370S+N401 D+S402Q+N411
L+F432V+L435A+T486V+S531R+Q595R+V821*+
S822*+P823*+D824*+H825*+G826*+K827*+
K828*;
D77G+T197I+N283F+K370S+N401D+S402Q+Y412F+
F432V+L435A+T486V+S531R+Q595R+V821*+
S822*+P823*+D824*+H825*+G826*+K827*+
K828*;
D77G+T197I+N283F+K370S+N401D+S402Q+F432V+
Q434E+L435A+T486V+S531R+Q595R+V821*+
S822*+P823*+D824*+H825*+G826*+K827*+
K828*;
D77G+T197I+N283F+K370S+N401 D+S402Q+F432V+
L435A+R443G+T486V+S531R+Q595R+V821*+
S822*+P823*+D824*+H825*+G826*+K827*+
K828*;
D77G+T197I+N283F+K370S+N401D+S402Q+F432V+
L435A+I446V+T486V+S531R+Q595R+V821*+
S822*+P823*+D824*+H825*+G826*+K827*+
K828*;
D77G+T197I+N283F+K370S+N401 D+S402Q+F432V+
L435A+T486V+Q498R+S531R+Q595R+V821*+
S822*+P823*+D824*+H825*+G826*+K827*+
K828*;
D77G+T197I+N283F+K370S+N401D+S402Q+F432V+
L435A+T486V+S531R+A533I+Q595R+V821*+
S822*+P823*+D824*+H825*+G826*+K827*+
K828*;
D77G+T197I+N283F+K370S+N401D+S402Q+F432V+
L435A+T486V+S531R+N541D+Q595R+V821*+
S822*+P823*+D824*+H825*+G826*+K827*+
K828*;
D77G+T197I+N283F+K370S+N401 D+S402Q+F432V+
L435A+T486V+S531R+A545I+Q595R+V821*+
S822*+P823*+D824*+H825*+G826*+K827*+
K828*;
D77G+T197I+N283F+K370S+N401 D+S402Q+F432V+
L435A+T486V+S531R+L580F+Q595R+V821*+
S822*+P823*+D824*+H825*+G826*+K827*+
K828*;
D77G+T197I+N283F+K370S+N401 D+S402Q+F432V+
L435A+H479N+T486V+S531R+Q595R+D688A+
V821*+S822*+P823*+D824*+H825*+G826*+
K827*+K828*;
D77G+T197I+N283F+D367N+K370S+N401D+S402Q+
F432V+L435A+T486V+S531R+Q595R+D688A+
V821*+S822*+P823*+D824*+H825*+G826*+
K827*+K828*;
D77G+T197I+N283F+K370S+S375H+N401D+S402Q+
F432V+L435A+T486V+S531R+Q595R+D688A+
V821*+S822*+P823*+D824*+H825*+G826*+
K827*+K828*;

D77G+T197I+N283F+K370S+N401D+S402Q+Y412F+
F432V+L435A+T486V+S531R+Q595R+D688A+
V821*+S822*+P823*+D824*+H825*+G826*+
K827*+K828*;
D77G+T197I+N283F+K370S+N401D+S402Q+F432V+
L435A+T486V+S531R+A533I+Q595R+D688A+
V821*+S822*+P823*+D824*+H825*+G826*+
K827*+K828*;
D77G+T197I+N283F+K370S+N401 D+S402Q+F432V+
L435A+T486V+S531R+L581F+Q595R+D688A+
V821*+S822*+P823*+D824*+H825*+G826*+
K827*+K828*;
D77G T197I N283F D367N K370S S375H N401D
S402Q F432V L435A T486V S531R Q595R D688A
V821*S822*P823*D824*H825*G826*K827*K828*;
D77G T197I N283F D367N K370S N401D S402Q
Y412F F432V L435A T486V S531R Q595R D688A
V821*S822*P823*D824*H825*G826*K827*K828*;
D77G T197I N283F D367N K370S N401D S402Q
F432V L435A T486V S531R A533I Q595R D688A
V821*S822*P823*D824*H825*G826*K827*K828*;
D77G T197I N283F D367N K370S N401D S402Q
F432V L435A T486V S531R L581F Q595R D688A
V821*S822*P823*D824*H825*G826*K827*K828*;
D77G T197I N283F K370S N401 D S402Q F432V
L435A T486V S531R Q595R V665I
V821*S822*P823*D824*H825*G826*K827*K828*;
D77G T197I N283F K370S N401 D S402Q F432V
L435A T486V S531R Q595R F700L
V821*S822*P823*D824*H825*G826*K827*K828*;
D77G T197I N283F K370S N401 D S402Q F432V
L435A T486V S531R Q595R P709I
V821*S822*P823*D824*H825*G826*K827*K828*;
D77G T197I N283F D367N K370S S375H N401D
S402Q Y412F F432V L435A T486V S531R Q595R
D688A
V821*S822*P823*D824*H825*G826*K827*K828*;
D77G T197I N283F D367N K370S S375H N401D
S402Q F432V L435A T486V S531R A533I Q595R
D688A
V821*S822*P823*D824*H825*G826*K827*K828*;
D77G T197I N283F D367N K370S S375H N401D
S402Q Y412F F432V L435A T486V S531R A533I
L581F Q595R D688A
V821*S822*P823*D824*H825*G826*K827*K828*;
D77G T197I N283F H321V D367N K370S S375H N401
D S402Q Y412F F432V Q434E L435A T486V S531R
A533I L581F Q595R D688A
V821*S822*P823*D824*H825*G826*K827*K828*;
D77G T197I N283F H321V D367N K370S S375H N401
D S402Q Y412F F432V L435A T486V Q498R S531R
A533I L581F Q595R D688A
V821*S822*P823*D824*H825*G826*K827*K828*;
D77G T197I N283F H321V D367N K370S S375H N401
D S402Q Y412F F432V L435A T486V S531R A533I
L581F Q595R D688A F700L
V821*S822*P823*D824*H825*G826*K827*K828*;
D77G T197I N283F H321V D367N K370S S375H N401
D S402Q Y412F F432V Q434E L435A T486V Q498R
S531R A533I L581F Q595R D688A F700L
V821*S822*P823*D824*H825*G826*K827*K828*;
F17Y D77G T197I N283F K370S N401D S402Q F432V
L435A T486V S531R Q595R
V821*S822*P823*D824*H825*G826*K827*K828*;
D77G T197I N283F K370S N401D S402Q F432V
L435A T486V S531R Q595R E804S
V821*S822*P823*D824*H825*G826*K827*K828*;

D77G T197I N283F K370S N401 D S402Q F432V L435A T486V S531R Q595R G811R V821*S822*P823*D824*H825*G826*K827*K828*;

D77G T197I N283F H321V K370S S375H N401 D S402Q Y412F F432V Q434E L435A H479N T486V Q498R S531R A533I L581F Q595R D688A F700L V821*S822*P823*D824*H825*G826*K827*K828*;

D77G A190I T197I N283F K370S S375H N401D S402Q Y412F F432V Q434E L435A H479N T486V Q498R S531R A533I L581F Q595R D688A F700L V821*S822*P823*D824*H825*G826*K827*K828*;

D77G T197I T262V N283F K370S S375H N401 D S402Q Y412F F432V Q434E L435A H479N T486V Q498R S531R A533I L581F Q595R D688A F700L V821*S822*P823*D824*H825*G826*K827*K828*; and D77G A190I T197I N283F H321V D367N K370S S375H N401D S402Q Y412F F432V Q434E L435A T486V Q498R S531R A533I L581F Q595R D688A F700L V821*S822*P823*D824*H825*G826*K827*K828*.

10. The variant pullulanase of any of the preceding paragraphs, comprising the substitutions N222P+Q252A+Q256R+N368G+N393A+Q431E+N610R+G624S+T631S+S632C, and optionally L432F.

11. The variant pullulanase of any of the preceding paragraphs, comprising the substitutions N222P+Q252A+Q256R+N368G+N393A+Q431E+N610R+G624S+T631S+S632C+N20G+Y28K+H80Y+Q187R+E310A+D311K+Q387L+Q459G+D586S+E699R+S798R, and optionally L432F.

12. The variant pullulanase of any of the preceding paragraphs, comprising the deletions P30*+V31*+N32*, and optionally Q29G.

13. The variant pullulanase of any of the preceding paragraphs, comprising the modifications Q29G+P30*+V31*+N32*+D57N+D58P+A195G+N202K+A345P+F456W+E560R, and optionally one, two, three, four or five of N197T, M402S, I460V, N479H, I514V.

14. The variant pullulanase of any of the preceding paragraphs, comprising the modifications N222P+Q252A+Q256R+N368G+N393A+Q431E++N610R+G624S+T631S+S632C+N20G+Y28K+H80Y+Q187R+E310A+D311K+Q387L+Q459G+D586S+E699R+S798R+Q29G+P30*+V31*+N32*+D57N+D58P+A195G+N202K+A345P+F456W+E560R, and optionally one, two, three, four, five or six of L432F, N197T, M402S, N479H, I460V, I514V.

15. The variant of any of the preceding paragraphs, wherein the variant comprises the substitutions X370S+X432V, particularly K370S+L,F432V, and optionally X492A,S.

16. The variant according to any of claims 1-15, wherein the variants have an increase in thermo-activity relative to a parent pullulanase, e.g., the pullulanase disclosed as SEQ ID NO: 3, of at least 5%, at least 10%, at least 20%, at least 25%, at least 30%, at least 35%, at least 40%, at least 50%, at least 60%, at least 70%, at least 80%, at least 90%, at least 100%, after enzymatic reaction of maltodextrin 2 hours at 85° C. or 30 min 91° C., and subsequent determination of digested maltodextrin fraction by PAHBAH assay at 55° C.

17. The variants of any of the preceding paragraphs, wherein the increase in thermo-stability determined as increased melting (denaturing) temperature compared to the parent pullulanase disclosed in SEQ ID NO: 3 using TSA assay is at least 0.3 degrees C., at least 0.4 degrees C., at least 0.5 degrees C., at least 0.6 degrees C., at least 0.8 degrees C., at least 1.0 degrees C., at least 1.2 degrees C., at least 1.5 degrees C., at least 2.0 degrees C., at least 2.5 degrees C., at least 3.0 degrees C., at least 3.5 degrees C., at least 4.0 degrees C., at least 4.5 degrees C., at least 5.0 degrees C.

18. A polynucleotide encoding the variant pullulanase of any of the paragraphs 1-17.

19. A nucleic acid construct or expression vector comprising the polynucleotide of paragraph 18 operably linked to one or more control sequences that direct the production of the polypeptide in an expression host.

20. A recombinant host cell comprising the polynucleotide of paragraph 18 operably linked to one or more control sequences that direct the production of the polypeptide.

21. A composition comprising the variant pullulanase of any of paragraphs 1-17 and a stabilizer.

22. The composition of paragraph 21, comprising an alpha-amylase.

23. The composition of paragraph 22, wherein the alpha-amylase is a bacterial alpha-amylase, particularly derived from *Bacillus* or *Exiguobacterium* species, such as, e.g., *Bacillus licheniformis* or *Bacillus stearothermophilus*.

24. The composition of any of paragraphs 22-23, wherein the alpha-amylase is from a strain of *Bacillus stearothermophilus*, in particular a variant of a *Bacillus stearothermophilus* alpha-amylase, such as the one shown in SEQ ID NO: 6.

25. The composition of any of paragraphs 23-24, wherein the *Bacillus stearothermophilus* alpha-amylase or variant thereof is truncated, preferably to have around 491 amino acids, such as from 480-495 amino acids.

26. The composition of any of paragraphs 23-25, wherein the *Bacillus stearothermophilus* alpha-amylase has a deletion at two positions within the range from positions 179 to 182, such as positions I181+G182, R179+G180, G180+I181, R179+I181, or G180+G182, preferably I181+G182, and optionally a N193F substitution, (using SEQ ID NO: 6 for numbering).

27. The composition of any of paragraphs 23-26, wherein the *Bacillus stearothermophilus* alpha-amylase has a substitution at position S242, preferably S242Q substitution.

28. The composition of any of paragraphs 23-27, wherein the *Bacillus stearothermophilus* alpha-amylase has a substitution at position E188, preferably E188P substitution.

29. The composition of any of paragraphs 21-28, wherein the alpha-amylase is selected from the group of *Bacillus stearothermophilus* alpha-amylase variants with the following mutations:

I181*+G182*+N193F+E129V+K177L+R179E;

I181*+G182*+N193F+V59A+Q89R+E129V+K177L+R179E+H208Y+K220P+N224L+Q254S;

I181*+G182*+N193F+V59A Q89R+E129V+K177L+R179E+Q254S+M284V; and

I181*+G182*+N193F+E129V+K177L+R179E+K220P+N224L+S242Q+Q254S (using SEQ ID NO: 6 for numbering).

30. The composition of any of paragraphs 21-29, wherein the alpha-amylase variant has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 6.
31. The composition of any of paragraphs 21-30, comprising a protease, particularly a serine protease or a metallo-protease, such as an S8 serine protease.
32. The composition of paragraph 31, comprising a protease, preferably a protease selected from a *Pyrococcus* sp protease, e.g. a *Pyrococcus furiosus* protease shown as SEQ ID NO: 8, or a protease having at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 8.
33. The composition of paragraph 31, comprising a protease, preferably a protease selected from a *Thermoascus* sp protease, e.g., a *Thermoascus aurantiacus* protease, particularly a variant of a *Thermoascus aurantiacus* protease, SEQ ID NO: 7, comprising one of the specific combinations of substitutions:
D79L+S87P+A112P+D142L;
D79L+S87P+D142L; or
A27K+D79L+Y82F+S87G+D104P+A112P+A126V+D142L, and wherein the protease has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 7.
34. The composition of paragraph 31, comprising a protease, preferably a protease selected from a *Palaeococcus* sp. S8 protease, particularly a *Palaeococcus ferrophilus* S8 protease shown as SEQ ID NO: 9 or a protease having at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 9.
35. The composition of any of paragraphs 21-34, comprising a thermo-stable glucoamylase, preferably a *Penicillium oxalicum* glucoamylase, more preferably a variant of a *Penicillium oxalicum* glucoamylase shown as SEQ ID NO: 16, comprising a K79V substitution (using SEQ ID NO: 16 for numbering), and further comprising one of the following mutations:
P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T,
and wherein, the glucoamylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 16.
36. A method of producing a variant pullulanase according to any of the paragraphs 1-17, comprising cultivating the host cell of paragraph 20 under conditions conducive for production of the polypeptide.
37. A process for producing a syrup from starch-containing material comprising the steps of:
a) liquefying the starch-containing material at a temperature above the initial gelatinization temperature using an alpha-amylase and a variant pullulanase of any of the paragraphs 1-17;
b) saccharifying using a glucoamylase.
38. A process for producing fermentation products from starch-containing material comprising the steps of:
a) liquefying the starch-containing material at a temperature above the initial gelatinization temperature using an alpha-amylase and a variant pullulanase of any of the paragraphs 1-17;
b) saccharifying using a glucoamylase;
c) fermenting using a fermenting organism.
39. The process of any of paragraphs 37-38, wherein the glucoamylase present and/or added in saccharification step b) and/or fermentation step c) is of fungal origin, preferably from a stain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Trametes*, preferably *T. cingulata*, or a strain of *Pycnoporus*, or a strain of *Gloeophyllum*, such as *G. sepiarium* or *G. trabeum*, or a strain of *Nigrofomes*.
40. The process of paragraph 39, wherein the glucoamylase is derived from *Talaromyces emersonii*, such as the one shown in SEQ ID NO: 10 herein.
41. The process of paragraph 40, wherein the glucoamylase is selected from the group consisting of:
(i) a glucoamylase comprising the polypeptide of SEQ ID NO: 10 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 10.
42. The process of paragraph 39, wherein the glucoamylase is derived from *Gloeophyllum sepiarium*, such as the one shown in SEQ ID NO: 12.
43. The process of paragraph 42, wherein the glucoamylase is selected from the group consisting of:
(i) a glucoamylase comprising the polypeptide of SEQ ID NO: 12;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12.
44. The process of paragraph 39, wherein the glucoamylase is derived from *Gloeophyllum trabeum* such as the one shown in SEQ ID NO: 13.
45. The process of claim 44, wherein the glucoamylase is selected from the group consisting of:
(i) a glucoamylase comprising the polypeptide of SEQ ID NO: 13;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 13.

46. The process of any of paragraphs 39-45, wherein a glucoamylase in combination with an alpha-amylase are present in saccharification and/or fermentation.
47. The process of paragraph 46, wherein the alpha-amylase present in saccharification and/or fermentation is of fungal or bacterial origin.
48. The process of paragraphs 46-47, wherein the alpha-amylase present and/or added in saccharification and/or fermentation is derived from a strain of the genus *Rhizomucor*, preferably a strain the *Rhizomucor pusillus*, such as a *Rhizomucor pusillus* alpha-amylase hybrid having an *Aspergillus niger* linker and starch-binding domain, such as the one included in SEQ ID NO: 15.
49. The process of any of paragraphs 46-48, wherein the alpha-amylase present in saccharification and/or fermentation is selected from the group consisting of:
(i) an alpha-amylase comprising the polypeptide of SEQ ID NO: 15;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15.
50. The process of paragraph 49, wherein the alpha-amylase comprises one or more of the following substitutions: G128D, D143N, preferably G128D+D143N, using SEQ ID NO: 15 for numbering.
51. The process of any of paragraphs 39-50, further comprising, prior to the liquefaction step a), the steps of:
i) reducing the particle size of the starch-containing material, preferably by dry milling;
ii) forming a slurry comprising the starch-containing material and water.
52. The process of any of paragraphs 37-51, wherein at least 50%, preferably at least 70%, more preferably at least 80%, especially at least 90% of the starch-containing material fit through a sieve with #6 screen.
53. The process of any of paragraphs 37-52, wherein the pH in liquefaction is between above 4.5-6.5, such as around 4.8, or a pH between 5.0-6.2, such as 5.0-6.0, such as between 5.0-5.5, such as around 5.2, such as around 5.4, such as around 5.6, such as around 5.8.
54. The process of any of paragraphs 37-53, wherein the temperature in liquefaction is above the initial gelatinization temperature, such as in the range from 70-100° C., such as between 75-95° C., such as between 75-90° C., preferably between 80-90° C., especially around 85° C.
55. The process of any of paragraphs 37-54, wherein a jet-cooking step is carried out before liquefaction in step a).
56. The process of paragraph 55, wherein the jet-cooking is carried out at a temperature between 110-145° C., preferably 120-140° C., such as 125-135° C., preferably around 130° C. for about 1-15 minutes, preferably for about 3-10 minutes, especially around about 5 minutes.
57. The process of any of paragraphs 37-56, wherein saccharification is carried out at a temperature from 20-75° C., preferably from 40-70° C., such as around 60° C., and at a pH between 4 and 5.
58. The process of any of paragraphs 38-57, wherein fermentation or simultaneous saccharification and fermentation (SSF) is carried out at a temperature from 25° C. to 40° C., such as from 28° C. to 35° C., such as from 30° C. to 34° C., preferably around about 32° C.
59. The process of any of paragraphs 38-58, wherein the fermentation product is recovered after fermentation, such as by distillation.
60. The process of any of paragraphs 38-59, wherein the fermentation product is an alcohol, preferably ethanol, especially fuel ethanol, potable ethanol and/or industrial ethanol.
61. The process of any of paragraphs 37-60, wherein the starch-containing starting material is whole grains.
62. The process of any of paragraphs 37-61, wherein the starch-containing material is derived from corn, wheat, barley, rye, milo, sago, cassava, manioc, tapioca, sorghum, rice or potatoes.
63. The process of any of paragraphs 37-62, wherein a composition of any of claims 21-35 is added/is present in liquefaction.
64. The process of any of paragraphs 38-63, wherein the fermenting organism is yeast, preferably a strain of *Saccharomyces*, especially a strain of *Saccharomyces cerevisiae*.
65. The recombinant host cell according to paragraph 20, wherein the host cell is a yeast host cell, particularly a strain of *Saccharomyces*, more particularly *Saccharomyces cerevisiae*.
66. A use of the host cell according to paragraph 20 or 65, in fermentation of hydrolysed starch.
67. A use of the variant pullulanase of any of the paragraphs 1-17 in a brewing process.
68. A use of the variant pullulanase of any of the paragraphs 1-17 in liquefaction of starch-containing material.
69. A method of producing a brewer's wort comprising adding to a mash, a pullulanase of any of the paragraphs 1-17.

The present invention is further described by the following examples that should not be construed as limiting the scope of the invention.

EXAMPLES

Enzymes

Protease PfuS: Protease derived from *Pyrococcus furiosus* shown in SEQ ID NO: 8.

Alpha-Amylase BE369 (AA369): *Bacillus stearothermophilus* alpha-amylase disclosed herein as SEQ ID NO: 5, and further having the mutations: I181*+G182*+N193F+V59A+Q89R+E129V+K177L+R179E+Q254S+M284V truncated to 491 amino acids (using SEQ ID NO: 6 for numbering).

Ms-trehalase: *Myceliophthora sepedonium* trehalase (SEQ ID NO: 30 in WO2016/205127) and SEQ ID NO: 17 herein.

Alpha-amylase blend AA: Blend comprising Alpha-amylase AA369, and protease PfuS (dosing: 2.1 µg EP/g DS AA369, 3.0 µg EP/g DS PfuS, where EP is enzyme protein and DS is total dry solids).

Glucoamylase A blend: Blend comprising *Talaromyces emersonii* glucoamylase (Te AMG) disclosed as SEQ ID NO: 34 in WO99/28448, *Trametes cingulata* glucoamylase (Tc AMG) disclosed as SEQ ID NO: 2 in WO 06/69289, and *Rhizomucor pusillus* alpha-amylase with *Aspergillus niger-glucoamylase* linker and starch binding domain (SBD) (Rp AA) disclosed in SEQ ID NO: 15 herein having the following substitutions G128D+D143N using SEQ ID NO: 15 for numbering (activity ratio in AGU:AGU:FAU-F is about 29:8:1).

Glucoamylase B blend: Same as glucoamylase blend A further having a cellulase composition containing a *Trichoderma reesei* cellulase preparation containing *Aspergillus fumigatus* cellobiohydrolase I (WO 2011/057140), *Aspergillus fumigatus* cellobiohydrolase II (WO 2011/057140), *Aspergillus fumigatus* beta-glucosidase variant (WO 2012/044915), and *Penicillium* sp. (*emersonii*) GH61 polypeptide (WO 2011/041397), and *Myceliophthora sepedonium* trehalase (SEQ ID NO: 30 in WO2016/205127) and SEQ ID NO: 17 herein (dosing: Te AMG 60 μg EP/gDS; Tc AMG 20 μg EP/gDS; Rp AA 11 μg EP/gDS; Cellulase composition 30 μg EP/gDS, Ms trehalase 1 μg EP/gDS).

Yeast: ETHANOL RED™ from Fermentis, USA

Assays

Protease Assays

1) Kinetic Suc-AAPF-pNA Assay:
   pNA substrate: Suc-AAPF-pNA (Bachem L-1400).
   Temperature: Room temperature (25° C.)
   Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 μl protease (diluted in 0.01% Triton X-100) was mixed with 100 μl assay buffer. The assay was started by adding 100 μl pNA substrate (50 mg dissolved in 1.0 ml DMSO and further diluted 45× with 0.01% Triton X-100). The increase in $OD_{405}$ was monitored as a measure of the protease activity.

2) Endpoint Suc-AAPF-pNA AK Assay:
   pNA substrate: Suc-AAPF-pNA (Bachem L-1400).
   Temperature: controlled (assay temperature).
   Assay buffer: 100 mM succinic acid, 100 mM HEPES, 100 mM CHES, 100 mM CABS, 1 mM $CaCl_2$, 150 mM KCl, 0.01% Triton X-100, pH 7.0.

200 μl pNA substrate (50 mg dissolved in 1.0 ml DMSO and further diluted 45× with the Assay buffer) were pipetted in an Eppendorf tube and placed on ice. 20 μl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath and adding 600 μl 500 mM Succinic acid/NaOH, pH 3.5. After mixing the Eppendorf tube by vortexing 20041 mixture was transferred to a microtiter plate. $OD_{405}$ was read as a measure of protease activity. A buffer blind was included in the assay (instead of enzyme).

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity Assays

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

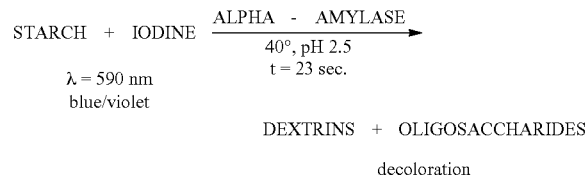

Standard Conditions/Reaction Conditions:
   Substrate: Soluble starch, approx. 0.17 g/L
   Buffer: Citrate, approx. 0.03 M
   Iodine (12): 0.03 g/L
   $CaCl_2$: 1.85 mM
   pH: 2.50±0.05
   Incubation 40° C.
Temperature:
   Reaction time: 23 seconds
   Wavelength: 590 nm
   Enzyme 0.025 AFAU/mL Concentration:
Enzyme working 0.01-0.04 AFAU/mL
Range:

A folder EB-SM-0259.02/01 describing this analytical method in more detail is available upon request to Novozymes A/S, Denmark, which folder is hereby included by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

pNP-G7 Assay

The alpha-amylase activity may be determined by a method employing the G7-pNP substrate. G7-pNP which is an abbreviation for 4,6-ethylidene($G_7$)-p-nitrophenyl ($G_7$)-□,D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at lambda=405 nm (400-420 nm.). Kits containing G7-pNP substrate and alpha-Glucosidase is manufactured by Roche/Hitachi (cat. No. 11876473).

Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H40)$~ (n=9-10))), 1 mM $CaCl_2$), pH8.0.

Procedure:

The amylase sample to be analyzed is diluted in dilution buffer to ensure the pH in the diluted sample is 7. The assay is performed by transferring 20 μl diluted enzyme samples to 96 well microtiter plate and adding 80 μl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

EnzChek® Assay:

For the determination of residual amylase activity an EnzChek® Ultra Amylase Assay Kit (E33651, Invitrogen, La Jolla, CA, USA) may be used.

The substrate is a corn starch derivative, DQ™ starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM $CaCl_2$, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM $CaCl_2$, pH 5.5). Immediately after incubation the enzyme is diluted to a concentration of 10-20 ng enzyme protein/ml in 100 mM acetate, 0.01% (W/v) TRITON® X100, 0.125 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Pullulanase Assays

Pullulanase Activity (NPUN) Assay

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

Phadebas Thermostability Assay

The culture supernatants containing desired enzymes was mixed with same volume of pH 5.0 400 mM NaOAc buffer.

Twenty microliter of this mixture was dispensed into either 96-well plate or 8-strip PCR tube, and then heated by thermal cycler at various temperatures for 30 min. Those samples were mixed with 100 μl of substrate solution containing 2% (w/v) phadebas [magle life science] in pH 5.0 200 mM NaOAc buffer, and incubated at 70° C. for 30 min for enzymatic reaction. After the reaction, 50 μl of 18% Acetic acid was added to stop the reaction. Eighty microliter of reaction supernatant was taken out and its $OD_{600}$ value was read by photometer to evaluate the enzyme activity.

Phadebas Thermoprofile Assay

The culture supernatants containing desired enzymes was mixed with same volume of pH 5.0 400 mM NaOAc buffer. Twenty microliter of this mixture was dispensed into 96-well plate or 8-strip PCR tubes, and then mixed with 100 μl of substrate solution containing 2% (w/v) phadebas [magle life science] in pH 5.0 200 mM NaOAc buffer. Those samples were incubated at various temperatures for 30 min for enzymatic reaction. After the reaction, 50 μl of 18% Acetic acid was added to stop the reaction. Eighty microliter of reaction supernatant was taken out and its $OD_{600}$ value was read by photometer to evaluate the enzyme activity.

Example 1: Construction of Pullulanase Libraries

Pullulanase Libraries were Constructed as Follows.

A forward or reverse primer having NNK or desired mutation(s) at target site(s) with 15 bp overlaps each other were designed. Inverse PCR, which means amplification of entire plasmid DNA sequences by inversely directed primers, were carried out with appropriate template plasmid DNA (e.g. plasmid DNA containing P604 encoding gene) by the following conditions. The resultant PCR fragments were purified by QIAquick Gel extraction kit [QIAGEN], and then introduced into *Escherichia coli* DH5a Competent HIGH [TOYOBO]. The plasmid DNAs were extracted from *E. coli* transformants by MagExtractor plasmid extraction kit [TOYOBO], and then introduced into *B. subtilis* competent cells.

PCR Reaction Mix:
PrimeSTAR Max DNA Polymerase [TaKaRa]
  Total 25 μl
  1.0 μl Template DNA (1 ng/μl)
  9.5 μl $H_2O$
  12.5 μl 2× PrimeSTAR Max pre-mix
  1.0 μl Forward primer (5 μM)
  1.0 μl Reverse primer (5 μM)
PCR Program:
  98° C./2 min
  25× (98° C./10 sec, 60° C./15 sec, 72° C./2 min)
  10° C./hold Example 2: Screening for Better Thermostability

*B. subtilis* libraries constructed as in EXAMPLE 1 were fermented in either 96-well or 24-well MTP containing 10R-av-30C medium (6.0 g/L $(NH_4)_2HPO_4$, 26 g/L Bacto pepton, 1.2 g/L $MgSO_4 \cdot 7H_2O$, 12 g/L $KH_2PO_4$, 5.0 g/L $Na_2HPO_4$, 1.8 g/L $K_2SO_4$, 0.1 g/L $CaCl_2 \cdot 2H_2O$, 33 g/L glucose, 4.9 mg/L $MnSO_4 \cdot 5H_2O$, 19.7 mg/L $FeSO_4 \cdot 7H_2O$, 1.0 mg/L $CuSO_4 \cdot 5H_2O$, 3.0 mg/L $ZnCl_2$, 196 mg/L Citric acid) with 8.0 mg/L chloramphenicol at 800 rpm, 37C, overnight. Then, pullulanase activities in culture supernatants were measured at several temperatures by Phadebas assay described as follows.

Phadebas Thermostability Assay

The culture supernatants containing desired enzymes was mixed with same volume of pH 5.0 400 mM NaOAc buffer. Twenty microliter of this mixture was dispensed into either 96-well plate or 8-strip PCR tube, and then heated by thermal cycler at various temperatures for 30 min. Those samples were mixed with 100 μl of substrate solution containing 2% (w/v) phadebas [magle life science] in pH 5.0 200 mM NaOAc buffer, and incubated at 70° C. for 30 min for enzymatic reaction. After the reaction, 50 μl of 18% Acetic acid was added to stop the reaction. Eighty microliter of reaction supernatant was taken out and its $OD_{600}$ value was read by photometer to evaluate the enzyme activity.

Phadebas Thermoprofile Assay

The culture supernatants containing desired enzymes was mixed with same volume of pH 5.0 400 mM NaOAc buffer. Twenty microliter of this mixture was dispensed into 96-well plate or 8-strip PCR tubes, and then mixed with 100 μl of substrate solution containing 2% (w/v) phadebas [magle life science] in pH 5.0 200 mM NaOAc buffer. Those samples were incubated at various temperatures for 30 min for enzymatic reaction. After the reaction, 50 μl of 18% Acetic acid was added to stop the reaction. Eighty microliter of reaction supernatant was taken out and its $OD_{600}$ value was read by photometer to evaluate the enzyme activity.

PAHBAH-Maltodextrin (DE3) Assay

Substrate Solution
  1 g maltodextrin (pindex100 from MATSUTANI chemical industry Co., Ltd.)
  5 ml 50 mM sodium acetate buffer, pH 5
PAHBAH solution
  0.0552 g Bismuth (III)-acetate
  0.2 g PAHBAH
  0.5 g Potassium sodium tartrate, tetrahydrate
  10 ml 500 mM NaOH Ten ul of enzyme samples were mixed with 110 ul of substrate solution and incubated at set temperatures for 2 hours (85° C.) or 30 min (91° C.). Ten ul of 0.5 N NaOH was added to stop reaction and cooled the tubes to 55° C. The reaction mixtures were diluted 40-fold with 50 mM sodium acetate buffer, pH 5. Fourty ul of PAHBAH solution was added to 120 ul of diluted mixtures, incubated for another 20 min at 55° C. and the absorbance at A405 was read.

TABLE 1a

List of the relative activity of pullulanase variants when compared with their parents (P604 or P609)

|  | <Thermostability> Relative activity of 81.5° C./80° C. (%) | <Thermoprofile> Relative activity of 81.5° C./80° C. (%) |
|---|---|---|
| P604 | 43% | 56% |
| P609 | 58% | 57% |

|  | <Thermostability> Relative activity of 81° C./80° C. (%) | <Thermoprofile> Relative activity of 81.5° C./70° C. (%) |
|---|---|---|
| P609 | 50% | 39% |
| P624 | 52% | 34% |
| P625 | 55% | 49% |
| P629 | 69% | 39% |

TABLE 1a-continued

List of the relative activity of pullulanase variants when compared with their parents (P604 or P609)

| | <Thermostability> Relative activity of 81° C./80° C. (%) | <Thermoprofile> Relative activity of 81.5°/80° C. (%) |
|---|---|---|
| P604 | 38% | 48% |
| P609 | 48% | 55% |
| P630 | 53% | 59% |
| P631 | 71% | 83% |
| P632 | 67% | 73% |

| | <Thermostability> Relative activity of 81° C./70° C. (%) | |
|---|---|---|
| P604 | 66% | |
| P633 | 78% | |
| P634 | 75% | |
| P635 | 71% | |

| | <Thermostability> Relative activity of 81° C./70° C. (%) | |
|---|---|---|
| P609 | 60% | |
| P638 | 68% | |
| P641 | 61% | |
| P643 | 54% | |
| P644 | 66% | |

| | <Thermostability> Relative activity of 83° C./70° C. (%) | <Thermoprofile> Relative activity of 81.5°/80° C. (%) |
|---|---|---|
| P609 | 10% | 32% |
| P639 | 46% | 59% |
| P640 | 24% | 44% |

| | <Thermostability> Relative activity of 81° C./80° C. (%) | <Thermoprofile> Relative activity of 81.5°/80° C. (%) |
|---|---|---|
| P609 | 28% | 24% |
| P645 | 42% | 15% |
| P646 | 35% | 21% |

TABLE 1b

List of the relative activity of pullulanase variants when compared with their parents (P632)

| | <Thermostability> Relative activity of 83° C./70° C. (%) |
|---|---|
| P632 | 12% |
| P648 | 19% |
| P649 | 19% |
| P650 | 24% |
| P651 | 28% |
| P652 | 24% |
| P653 | 26% |
| P654 | 20% |
| P655 | 16% |
| P656 | 46% |
| P657 | 26% |

TABLE 1c

List of the relative activity of pullulanase variants when compared with their parents (P656)

| | <Thermostability> Relative activity of 83° C./70° C. (%) |
|---|---|
| P656 | 53% |
| P675 | 61% |
| P676 | 57% |
| P677 | 58% |
| P678 | 62% |
| P679 | 63% |
| P680 | 63% |
| P681 | 62% |
| P682 | 64% |
| P656 | 15% |
| P683 | 25% |
| P684 | 30% |
| P685 | 38% |
| P698 | 43% |

TABLE 1d

List of the relative activity of pullulanase variants when compared with their parents (P685 or P698)

| | <Thermostability> Relative activity of 84° C./70° C. (%) |
|---|---|
| P685 | 19% |
| P698 | 21% |
| P699 | 24% |
| P700 | 15% |
| | <Thermostability> Relative activity of 84° C./70° C. (%) |
| P685 | 11% |
| P698 | 14% |
| P703 | 13% |
| P725 | 16% |
| | <Thermostability> Relative activity of 83° C./70° C. (%) |
| P685 | 32% |
| P698 | 38% |
| P718 | 13% |
| P719 | 30% |

TABLE 1e

List of the relative activity of pullulanase variants when compared with their parents (P719)

| | <Thermostability> Relative activity of 83° C./80° C. (%) | <Thermoprofile> Relative activity of 83° C./80° C. (%) |
|---|---|---|
| P719 | 43% | 34% |
| P731 | 44% | 46% |
| P741 | 64% | 36% |

| | <Thermostability> Relative activity of 83° C./70° C. (%) | |
|---|---|---|
| P719 | 9% | |
| P753 | 12% | |
| P765 | 22% | |
| P766 | 28% | |

TABLE 1e-continued

List of the relative activity of pullulanase variants when compared with their parents (P719)

|  | <Thermostability> Relative activity of 84° C./80° C. (%) | <Thermoprofile> Relative activity of 85° C./80° C. (%) |
|---|---|---|
| P719 | not tested | 15% |
| P753 | 7% | 22% |
| P765 | 15% | 41% |
| P766 | 16% | 23% |
| P778 | 12% | 30% |
| P779 | 24% | 35% |
| P781 | 24% | 31% |
| P782 | 18% | 36% |
| P783 | 22% | 33% |

TABLE 1f

List of the relative activity of pullulanase variants when compared with their parents (P781)

|  | <Thermostability> Relative activity of 85° C./80° C. (%) | <Thermoprofile> Relative activity of 85° C./83° C. (%) |
|---|---|---|
| P781 | 4% | 49% |
| P787 | 7% | 50% |
| P789 | 5% | 40% |
| P791 | 3% | 47% |
| P795 | 17% | 49% |
| P797 | 14% | 54% |

TABLE 1g

List of the relative activity of pullulanase variants when compared with their parents (P797)

|  | <Thermostability> Relative activity of 84° C./80° C. (%) |
|---|---|
| P797 | 12% |
| P823 | 36% |
| P845 | 22% |
| P846 | 17% |
| P847 | 37% |
| P848 | 13% |
| P855 | 16% |
| P856 | 32% |
| P861 | 16% |

|  | <Thermostability> Relative activity of 84° C./80° C. (%) | <Thermoprofile> Relative activity of 85° C./84° C. (%) |
|---|---|---|
| P797 | 15% | 39% |
| P865 | 14% | 40% |
| P866 | 11% | 45% |
| P876 | 17% | 52% |
| P881 | 20% | 37% |
| P882 | 6% | 45% |
| P883 | 7% | 55% |
| P893 | 25% | 48% |

|  | <Thermostability> Relative activity of 84° C./80° C. (%) |
|---|---|
| P797 | 3% |
| P823 | 15% |
| P897 | 13% |
| P898 | 17% |
| P899 | 31% |
| P900 | 42% |
| P901 | 40% |
| P902 | 45% |

TABLE 1g-continued

List of the relative activity of pullulanase variants when compared with their parents (P797)

| P903 | 42% |
|---|---|
| P905 | 31% |
| P906 | 33% |
| P907 | 45% |
| P940 | 34% |
| P941 | 41% |

|  | <Thermostability> Relative activity of 84° C./80° C. (%) | <Thermoprofile> Relative activity of 84° C./80° C. (%) |
|---|---|---|
| P797 | 20% | 33% |
| P922 | 22% | 28% |
| P931 | 26% | 37% |
| P933 | 25% | 30% |

|  | <Thermostability> Relative activity of 86° C./85° C. (%) | <Thermoprofile> Relative activity of 85° C./80° C. (%) |
|---|---|---|
| P797 | 2% | 53% |
| P823 | 9% | 51% |
| P901 | 18% | 55% |
| P944 | 63% | 64% |

|  | <Thermostability> Relative activity of 84° C./80° C. (%) | <Thermoprofile> Relative activity of 85° C./84° C. (%) |
|---|---|---|
| P797 | 11% | 49% |
| P995 | 9% | 52% |
| P1025 | 8% | 58% |
| P1026 | 19% | 54% |

TABLE 1h

List of the relative activity of pullulanase variants when compared with their parents (P944 or P993)

|  | <Thermostability> Relative activity of 87° C./86° C. (%) | <Thermoprofile> Relative activity of 86° C./80° C. (%) |
|---|---|---|
| P944 | 17% | 15% |
| P990 | 24% | 18% |
| P991 | 24% | 16% |
| P992 | 28% | 19% |
| P993 | 25% | 16% |

|  | <Thermostability> Relative activity of 85° C./80° C. (%) | <Thermoprofile> Relative activity of 86° C./85° C. (%) |
|---|---|---|
| P993 | 66% | 45% |
| P1031 | 74% | 38% |
| P1033 | 79% | 53% |
| P1034 | 65% | 40% |

|  | <Thermostability> Relative activity of 87° C./85° C. (%) | <Thermoprofile> Relative activity of 86° C./80° C. (%) |
|---|---|---|
| P993 | 49% | 73% |
| P1033 | 59% | 86% |
| P1037 | 71% | 95% |

TABLE 2

| | Substitutions of thermostabilized variants on P604 |
|---|---|
| JPUL609 | K370S |
| JPUL624 | Q279R K370S |
| JPUL625 | H321E K370S |
| JPUL629 | K370S V821* S822* P823* D824* H825* G826* K827* K828* |
| JPUL630 | K370S Q399N |
| JPUL631 | K370S N401D |
| JPUL632 | K370S F432V |
| JPUL633 | V196T K370S |
| JPUL634 | V196C K370S |
| JPUL635 | T197I K370S |
| JPUL638 | K370S V460E |
| JPUL639 | K370S T486A |
| JPUL640 | K370S T486V |
| JPUL641 | K370S I490L |
| JPUL643 | K370S V514A |
| JPUL644 | K370S T529L |
| JPUL645 | K370S S531R |
| JPUL646 | K370S Q595R |
| JPUL648 | H321E K370S F432V |
| JPUL649 | K370S F432V V821* S822* P823* D824* H825* G826* K827* K828* |
| JPUL650 | K370S Q399N F432V |
| JPUL651 | K370S N401D F432V |
| JPUL652 | V196T K370S F432V |
| JPUL653 | V196C K370S F432V |
| JPUL654 | T197I K370S F432V |
| JPUL655 | K370S F432V G459E |
| JPUL656 | K370S F432V T486A |
| JPUL657 | K370S F432V T486V |
| JPUL675 | V196T K370S F432V T486A |
| JPUL676 | T197I K370S F432V T486A |
| JPUL677 | V196T T197I K370S F432V T486A |
| JPUL678 | K370S Q399N F432V T486A |
| JPUL679 | K370S N401D F432V T486A |
| JPUL680 | K370S Q399N N401D F432V T486A |
| JPUL681 | K370S S531R F432V T486A |
| JPUL682 | K370S Q595R F432V T486A |
| JPUL683 | K370S F432V T486A S531R Q595R |
| JPUL684 | V196T T197I K370S Q399N N401D F432V T486A |
| JPUL685 | V196T T197I K370S Q399N N401D F432V T486A Q595R |
| JPUL698 | T197I K370S N401D F432V T486A S531R Q595R |
| JPUL699 | T197I K370S N401D F432V T486A S531R Q595R V821* S822* P823* D824* H825* G826* K827* K828* |
| JPUL700 | T197I K370S Q399N N401D F432V T486A Q595R |
| JPUL703 | S103K T197I K370S N401D F432V T486A S531R Q595R |
| JPUL718 | V196T T197I K370S Q399N N401D F432V T486V Q595R |
| JPUL719 | T197I K370S N401D F432V T486V S531R Q595R |
| JPUL725 | V196T T197I K370S Q399N N401D F432V T486A S531R Q595R |
| JPUL731 | D77G T197I K370S N401D F432V T486V S531R Q595R |
| JPUL741 | T197I K370S N401D S402Q F432V T486V S531R Q595R |
| JPUL753 | T197I N283F K370S N401D F432V T486V S531R Q595R |
| JPUL765 | T197I N283F K370S N401D S402Q F432V T486V S531R Q595R |
| JPUL766 | T197I N283F K370S N401D F432V L435A T486V S531R Q595R |
| JPUL778 | D77G T197I N283F K370S N401D S402Q F432V T486V S531R Q595R |
| JPUL779 | T197I N283F K370S N401D S402Q F432V L435A T486V S531R Q595R |
| JPUL781 | D77G T197I N283F K370S N401D S402Q F432V L435A T486V S531R Q595R |
| JPUL782 | T197I N283F K370S N401D S402Q F432V L435A T486V S531R Q595R D649A |
| JPUL783 | D77G T197I N283F K370S N401D S402Q F432V L435A T486V S531R Q595R D649A |
| JPUL787 | D77G Q106W T197I N283F K370S N401D S402Q F432V L435A T486V S531R Q595R |
| JPUL789 | D77G A107D T197I N283F K370S N401D S402Q F432V L435A T486V S531R Q595R |
| JPUL791 | D77G V196C T197I N283F K370S N401D S402Q F432V L435A T486V S531R Q595R |
| JPUL795 | D77G T197I N283F K370S N401D S402Q F432V L435A T486V S531R N583O Q595R |
| JPUL797 | D77G T197I N283F K370S N401D S402Q F432V L435A T486V S531R Q595R V821* S822* P823* D824* H825* G826* K827* K828* |
| JPUL823 | D77G T197I N283F K370S N401D S402Q F432V L435A T486V S531R Q595R D688A V821* S822* P823* D824* H825* G826* K827* K828* |
| JPUL845 | D77G T197I N283F D367G K370S N401D S402Q F432V L435A T486V S531R Q595R V821* S822* P823* D824* H825* G826* K827* K828* |
| JPUL846 | D77G T197I N283F D367N K370S N401D S402Q F432V L435A T486V S531R Q595R V821* S822* P823* D824* H825* G826* K827* K828* |
| JPUL847 | D77G T197I N283F K370S S375H N401D S402Q F432V L435A T486V S531R Q595R V821* S822* P823* D824* H825* G826* K827* K828* |
| JPUL848 | D77G T197I N283F K370S N382T N401D S402Q F432V L435A T486V S531R Q595R V821* S822* P823* D824* H825* G826* K827* K828* |

TABLE 2-continued

Substitutions of thermostabilized variants on P604

| | |
|---|---|
| JPUL855 | D77G T197I N283F K370S N401D S402Q N411L F432V L435A T486V S531R Q595R V821* S822* P823* D824* H825* G826* K827* K828* |
| JPUL856 | D77G T197I N283F K370S N401D S402Q Y412F F432V L435A T486V S531R Q595R V821* S822* P823* D824* H825* G826* K827* K828* |
| JPUL861 | D77G T197I N283F K370S N401D S402Q F432V Q434E L435A T486V S531R Q595R V821* S822* P823* D824* H825* G826* K827* K828* |
| JPUL865 | D77G T197I N283F K370S N401D S402Q F432V L435A R443G T486V S531R Q595R V821* S822* P823* D824* H825* G826* K827* K828* |
| JPUL866 | D77G T197I N283F K370S N401D S402Q F432V L435A I446V T486V S531R Q595R V821* S822* P823* D824* H825* G826* K827* K828* |
| JPUL876 | D77G T197I N283F K370S N401D 3402Q F432V L435A T486V Q498R S531R Q595R V821* S822* P823* D824* H825* G826* K827* K828* |
| JPUL881 | D77G T197I N283F K370S N401D S402Q F432V L435A T486V S531R A533I Q595R V821* S822* P823* D824* H825* G826* K827* K828* |
| JPUL882 | D77G T197I N283F K370S N401D S402Q F432V L435A T486V S531R N541D Q595R V821* S822* P823* D824* H825* G826* K827* K828* |
| JPUL883 | D77G T197I N283F K370S N401D S402Q F432V L435A T486V S531R A545I Q595R V821* S822* P823* D824* H825* G826* K827* K828* |
| JPUL893 | D77G T197I N283F K370S N401D S402Q F432V L435A T486V S531R L581F Q595R V821* S822* P823* D824* H825* G826* K827* K828* |
| JPUL897 | D77G T197I N283F K370S N401D S402Q F432V L435A H479N T486V S531R Q595R D688A V821* S822* P823* D824* H825* G826* K827* K828* |
| JPUL898 | D77G T197I N283F D367N K370S N401D S402Q F432V L435A T486V S531R Q595R D688A V821* S822* P823* D824* H825* G826* K827* K828* |
| JPUL899 | D77G T197I N283F K370S S375H N401D S402Q F432V L435A T486V S531R Q595R D688A V821* S822* P823* D824* H825* G826* K827* K828* |
| JPUL900 | D77G T197I N283F K370S N401D S402Q Y412F F432V L435A T486V S531R Q595R D688A V821* S822* P823* D824* H825* G826* K827* K828* |
| JPUL901 | D77G T197I N283F K370S N401D S402Q F432V L435A T486V S531R A533I Q595R D688A V821* S822* P823* D824* H825* G826* K827* K828* |
| JPUL902 | D77G T197I N283F K370S N401D S402Q F432V L435A T486V S531R L581F Q595R D688A V821* S822* P823* D824* H825* G826* K827* K828* |
| JPUL903 | D77G T197I N283F D367N K370S S375H N401D S402Q F432V L435A T486V S531R Q595R D688A V821* S822* P823* D824* H825* G826* K827* K828* |
| JPUL905 | D77G T197I N283F D367N K370S N401D S402Q Y412F F432V L435A T486V S531R Q595R D688A V821* S822* P823* D824* H825* G826* K827* K828* |
| JPUL906 | D77G T197I N283F D367N K370S N401D S402Q F432V L435A T486V S531R A533I Q595R D688A V821* S822* P823* D824* H825* G826* K827* K828* |
| JPUL907 | D77G T197I N283F D367N K370S N401D S402Q F432V L435A T486V S531R L581F Q595R D688A V821* S822* P823* D824* H825* G826* K827* K828* |
| JPUL922 | D77G T197I N283F K370S N401D S402Q F432V L435A T486V S531R Q595R V665I V821* S822* P823* D824* H825* G826* K827* K828* |
| JPUL931 | D77G T197I N283F K370S N401D S402Q F432V L435A T486V S531R Q595R F700L V821* S822* P823* D824* H825* G826* K827* K828* |
| JPUL933 | D77G T197I N283F K370S N401D S402Q F432V L435A T486V S531R Q595R P709I V821* S822* P823* D824* H825* G826* K827* K828* |
| JPUL940 | D77G T197I N283F D367N K370S S375H N401D S402Q Y412F F432V L435A T486V S531R Q595R D688A V821* S822* P823* D824* H825* G826* K827* K828* |
| JPUL941 | D77G T197I N283F D367N K370S S375H N401D S402Q F432V L435A T486V S531R A533I Q595R D688A V821* S822* P823* D824* H825* G826* K827* K828* |
| JPUL944 | D77G T197I N283F D367N K370S S375H N401D S402Q Y412F F432V L435A T486V S531R A533I L581F Q595R D688A V821* S822* P823* D824* H825* G826* K827* K828* |
| JPUL990 | D77G T197I N283F H321V D367N K370S S375H N401D S402Q Y412F F432V Q434E L435A T486V S531R A533I L581F Q595R D688A V821* S822* P823* D824* H825* G826* K827* K828* |
| JPUL991 | D77G T197I N283F H321V D367N K370S S375H N401D S402Q Y412F F432V L435A T486V Q498R S531R A533I L581F Q595R D688A V821* S822* P823* D824* H825* G826* K827* K828* |
| JPUL992 | D77G T197I N283F H321V D367N K370S S375H N401D S402Q Y412F F432V L435A T486V S531R A533I L581F Q595R D688A F700L V821* S822* P823* D824* H825* G826* K827* K828* |
| JPUL993 | D77G T197I N283F H321V D367N K370S S375H N401D S402Q Y412F F432V Q434E L435A T486V Q498R S531R A533I L581F Q595R D688A F700L V821* S822* P823* D824* H825* G826* K827* K828* |
| JPUL995 | F17Y D77G T197I N283F K370S N401D S402Q F432V L435A T486V S531R Q595R V821* S822* P823* D824* H825* G826* K827* K828* |
| JPUL1025 | D77G T197I N283F K370S N401D S402Q F432V L435A T486V S531R Q595R E804S V821* S822* P823* D824* H825* G826* K827* K828* |
| JPUL1026 | D77G T197I N283F K370S N401D S402Q F432V L435A T486V S531R Q595R G811R V821* S822* P823* D824* H825* G826* K827* K828* |
| JPUL1031 | D77G T197I N283F H321V K370S S375H N401D S402Q Y412F F432V Q434E L435A H479N T486V Q498R S531R A533I L581F Q595R D688A F700L V821* S822* P823* D824* H825* G826* K827* K828* |

TABLE 2-continued

Substitutions of thermostabilized variants on P604

JPUL1033  D77G A190I T197I N283F K370S S375H N401D S402Q Y412F F432V Q434E
          L435A H479N T486V Q498R S531R A533I L581F Q595R D688A F700L V821*
          S822* P823* D824* H825* G826* K827* K828*
JPUL1034  D77G T197I T262V N283F K370S S375H N401D S402Q Y412F F432V Q434E
          L435A H479N T486V Q498R S531R A533I L581F Q595R D688A F700L V821*
          S822* P823* D824* H825* G826* K827* K828*
JPUL1037  D77G A190I T197I N283F H321V D367N K370S S375H N401D S402Q Y412F
          F432V Q434E L435A T486V Q498R S531R A533I L581F Q595R D688A F700L
          V821* S822* P823* D824* H825* G826* K827* K828*

Example 3: Fermentation of the Bacillus Strains

B. subtilis strains were fermented on a rotary shaking table in 500 ml baffled flasks containing 100 ml 10R-av-30C with 8 mg/L chloramphenicol at 200 rpm, 37° C. The culture broth was centrifuged (10,000×g, 20 min) and the supernatant was carefully decanted from the precipitates.

Example 4: Purification of Pullulanases

Pullulanase variant was purified through two steps of ammonium sulfate precipitation and cation exchange chromatography. Finally, the sample was desalted and buffer exchanged using a centrifugal filter unit (Vivaspin Turbo 15, Sartorius) with 20 mM sodium acetate buffer pH 4.5. Enzyme concentrations were determined by A280 value.

Example 5: Thermo-Stability Determination (TSA)

Purified enzyme was diluted with 50 mM sodium acetate buffer pH 4.5 to 0.5 mg/ml and mixed with equal volume of SYPRO Orange (Invitrogen) diluted with Milli-Q water. Eighteen ul of mixture solution were transfer to LightCycler 480 Multiwell Plate 384 (Roche Diagnostics) and the plate was sealed.
Equipment Parameters of TSA:
Apparatus: LightCycler 480 Real-Time PCR System (Roche Applied Science)
  Scan rate: 0.02° C./sec
  Scan range: 37-96° C.
  Integration time: 1.0 sec
  Excitation wave length 465 nm
  Emission wave length 580 nm
The obtained fluorescence signal was normalized into a range of 0 and 1. The Td2 was defined as the temperature at the maximum signal intensity.
The thermo-stability improvements are listed in TABLE 3 with Td2 of JPUL604 as 0.

Example 6: Pullulanase Assay

PAHBAH-Maltodextrin (DE3) Assay
Substrate Solution
  1 g maltodextrin (pindex100 from MATSUTANI chemical industry Co., Ltd.)
  5 ml 50 mM sodium acetate buffer, pH 5
PAHBAH solution
  0.0552 g Bismuth (III)-acetate
  0.2 g PAHBAH
  0.5 g Potassium sodium tartrate, tetrahydrate
  10 ml 500 mM NaOH
Ten µl of enzyme samples were mixed with 110 µl of substrate solution and incubated at set temperatures for 2 hours (8500) or 30 min (9100). Ten ul of 0.5 N NaOH was added to stop reaction and cooled the tubes to 5500. The reaction mixtures were diluted 40-fold with 50 mM sodium acetate buffer, pH 5. 40 µl of PAHBAH solution was added to 120 µl of diluted mixtures, incubated for another 20 min at 55° C. and the absorbance at A405 was read.

The activities are listed in TABLE 3 as relative activity to that of JPUL604.

TABLE 3

| JPUL # | Increase in Td2 [° C.] (JPUL604 as 0) | Activity at 85° C. (Relative to JPUL604) | Activity at 91° C. (Relative to JPUL604) |
|---|---|---|---|
| P609 | 0 | 100% | 127% |
| P624 | — | — | — |
| P625 | −0.16 | 97% | — |
| P629 | 0.12 | 118% | — |
| P630 | 0.54 | 137% | — |
| P631 | 0.69 | 129% | — |
| P632 | 0.96 | 140% | — |
| P633 | — | — | — |
| P634 | 0.25 | 130% | — |
| P635 | — | — | — |
| P638 | −0.69 | 104% | — |
| P639 | 1.56 | 93% | — |
| P640 | 0.32 | 127% | — |
| P641 | −0.42 | 108% | — |
| P643 | −0.06 | 120% | — |
| P644 | −0.51 | 109% | — |
| P645 | 0.19 | 126% | — |
| P646 | 0.45 | 136% | — |
| P648 | — | — | — |
| P649 | — | — | — |
| P650 | — | — | — |
| P651 | — | — | — |
| P652 | — | — | — |
| P653 | — | — | — |
| P654 | 1.16 | 119% | — |
| P655 | — | — | — |
| P656 | 2.68 | 99% | 105% |
| P657 | 1.60 | 122% | 92% |
| P675 | — | — | — |
| P676 | 2.98 | 132% | 44% |
| P677 | — | — | — |
| P678 | 3.41 | 132% | 56% |
| P679 | 3.50 | 133% | 103% |
| P680 | 3.53 | 139% | 111% |
| P681 | 3.29 | 119% | 63% |
| P682 | 3.38 | 134% | 43% |
| P683 | 3.96 | 149% | 84% |
| P684 | 3.56 | 157% | 123% |
| P685 | 4.18 | 129% | 147% |
| P698 | 4.42 | 130% | 136% |
| P699 | 4.07 | 126% | — |
| P700 | 4.07 | 135% | — |
| P703 | 4.24 | 133% | — |
| P704 | 3.63 | 119% | — |
| P718 | 2.68 | 183% | 225% |
| P719 | 2.87 | 185% | 238% |
| P725 | 4.00 | 135% | — |
| P730 | 2.80 | 189% | — |
| P731 | 3.01 | 181% | — |
| P738 | 2.62 | 173% | — |

TABLE 3-continued

| JPUL # | Increase in Td2 [° C.] (JPUL604 as 0) | Activity at 85° C. (Relative to JPUL604) | Activity at 91° C. (Relative to JPUL604) |
|---|---|---|---|
| P740 | 1.99 | 151% | — |
| P741 | 3.24 | 227% | — |
| P743 | 2.49 | 180% | — |
| P745 | 2.80 | 179% | — |
| P746 | 3.21 | 187% | — |
| P747 | 2.58 | 182% | — |
| P753 | 3.39 | 204% | 217% |
| P755 | 2.94 | 194% | — |
| P762 | 3.19 | 187% | — |
| P763 | 3.09 | 204% | — |
| P764 | 3.15 | 211% | — |
| P765 | 3.52 | 216% | 242% |
| P766 | 2.97 | 229% | 226% |
| P767 | 3.32 | 205% | 207% |
| P771 | 3.00 | 196% | 210% |
| P776 | −0.06 | 88% | — |
| P777 | 3.37 | 197% | 224% |
| P778 | 4.04 | 225% | 223% |
| P779 | 3.70 | 237% | 233% |
| P780 | 3.88 | 223% | 243% |
| P781 | 3.74 | 215% | |
| P782 | 3.52 | 234% | 241% |
| P783 | 3.70 | 220% | 231% |
| P787 | 3.65 | 212% | 286% |
| P789 | 3.75 | 198% | 243% |
| P791 | 3.68 | 233% | 277% |
| P794 | 5.28 | 117% | 38% |
| P795 | 3.79 | 229% | 215% |
| P797 | 3.96 | 251% | 240% |
| P812 | 3.59 | 258% | 244% |
| P818 | 3.95 | 198% | 183% |
| P823 | 5.18 | 235% | 257% |
| P845 | 4.35 | 258% | 266% |
| P846 | 4.35 | 264% | 260% |
| P847 | 4.29 | 297% | 271% |
| P848 | 4.19 | 270% | 218% |
| P855 | 4.19 | 261% | 225% |
| P856 | 4.99 | 279% | 248% |
| P861 | 4.10 | 282% | 215% |
| P865 | 3.87 | — | 231% |
| P866 | 3.72 | — | 221% |
| P876 | 3.93 | — | 246% |
| P881 | 3.96 | — | 257% |
| P882 | 3.20 | — | 207% |
| P883 | 3.60 | — | 207% |
| P893 | 4.18 | — | 226% |
| P897 | 4.97 | — | 309% |
| P900 | — | — | — |
| P901 | 5.44 | — | 297% |
| P903 | 5.82 | — | 362% |
| P907 | 6.88 | — | 385% |
| P922 | 4.05 | — | 184% |
| P931 | 4.91 | — | 227% |
| P933 | 4.17 | — | 208% |
| P941 | 6.47 | — | 300% |
| P942 | — | — | 363% |
| P943 | — | — | 318% |
| P944 | 6.81 | — | 348% |
| P946 | 6.88 | — | 354% |
| P973 | — | — | — |
| P989 | — | — | — |
| P990 | 7.29 | — | 330% |
| P991 | 7.13 | — | 228% |
| P992 | 7.71 | — | 317% |
| P993 | 7.65 | — | 364% |
| P994 | 7.29 | — | 331% |
| P1025 | 3.83 | — | 236% |
| P1026 | 4.24 | — | 244% |
| P1031 | 7.03 | — | 348% |
| P1033 | 7.88 | — | 422% |
| P1034 | 7.00 | — | 335% |
| P1037 | 8.45 | — | 482% |

Example 7. Application of Selected Variants in a Starch to Ethanol Process

Effect of JPUL604, JPUL609, JPUL719 variants enzyme addition in liquefaction process for increasing ethanol titer in simultaneous saccharification and fermentation process.

Liquefaction was carried out in a metal canister using Labomat BFA-24 (Mathis, Concord, NC). In the canister was added 37.2 g of industrial produced ground corn (88.7% dry solids) and 62.7 g tap water and mixed well. The target dry solid was about 33% DS. pH was adjusted to pH 5.0 and dry solid was measured using moisture balance (Mettler-Toledo). Alpha-Amylase BE369 was dosed 0.016% (w/w) into the corn slurry with or without appropriate amount of JPUL variant enzymes as shown in the table below. Total weight of corn slurry mixture was 100 g. As control, only Alpha-Amylase BE369 was added without addition of JPUL enzyme. Liquefaction took place in the Labomat chamber at 85° C. for 2 hr. After liquefaction, canister was cooled in ice-bath to room temperature and the respective liquefied mash was transferred to a container following by supplemented with 3 ppm of penicillin and 1000 ppm of urea. Simultaneous saccharification and fermentation (SSF) was performed via mini-scale fermentations using Ethanol Red™ yeast. Approximately 5 g of liquefied corn mash above was added to 15 ml tube vials. Each vial was dosed with 0.6 AGU/gDS of commercial glucoamylase Glucoamylase B blend followed by addition of 100 micro liters hydrated yeast per 5 g slurry. Actual glucoamylase dosage was based on the exact weight of liquefied corn mash in each vial. Vials were incubated at 32° C. Four replicates were used with 52 hours time point fermentation. Fermentation was stopped by addition of 50 micro liters of 40% $H_2SO_4$, follow by centrifuging, and filtering through a 0.2 micrometer filter. Ethanol and oligosaccharides concentration were determined using HPLC.

TABLE 4

| Treatments | Alpha-Amylase BE369 (%, w/w) | JPUL dosage (μg/g DS) |
|---|---|---|
| 1. Control | 0.016 | — |
| 2. JPUL604 | 0.016 | 20 |
| 3. JPUL609 | 0.016 | 10 |
| 4. JPUL719 | 0.016 | 10 |

Result

As shown in result table below, addition of JPUL variant enzymes together with Alpha-Amylase BE369 in liquefaction increased ethanol yield compared to control.

TABLE

| Treatments | Average ethanol concentration (g/l) |
|---|---|
| 1. Control | 133.32 |
| 2. JPUL604 | 133.34 |
| 3. JPUL609 | 133.49 |
| 4. JPUL719 | 133.50 |

The invention claimed is:

1. A variant pullulanase, having increased thermo-stability and/or increased thermo-activity compared to a parent pullulanase, comprising a substitution at least at one position selected from a position corresponding to positions 432 486, 370, 17, 77, 103, 106, 107, 190, 196, 197, 262, 279, 283, 321, 367, 375, 382, 399, 401, 402, 411, 412, 434, 435, 443, 446, 459, 460, 479, 490, 498, 514, 529, 531, 533, 541, 545, 581, 583, 595, 649, 665, 688, 700, 709, 804, and 811 of SEQ ID NO: 1, and a deletion of one or more amino acids at positions 821, 822, 823, 824, 825, 826, 827, and 828, wherein the variant has pullulanase activity, and wherein the variant has at least 85% but less than 100% sequence identity to a parent pullulanase selected from the group consisting of SEQ ID NO: 1, SEQ ID NO: 3, SEQ ID NO: 4, SEQ ID NO: 5.

2. The variant pullulanase of claim 1, comprising a substitution at a position corresponding to position 432 of SEQ ID NO: 1, wherein the variant pullulanase comprises valine in position 432 using SEQ ID NO: 1 for numbering, wherein the variant has pullulanase activity, and wherein the variant has at least 85% but less than 100% sequence identity to a parent pullulanase selected from the group consisting of SEQ ID NO: 1, SEQ ID NO: 3, SEQ ID NO: 4, SEQ ID NO: 5.

3. The variant pullulanase of claim 1, comprising a substitution at a position corresponding to position 486 of SEQ ID NO: 1, wherein the variant pullulanase comprises alanine or valine in position 486 using SEQ ID NO: 1 for numbering, wherein the variant has pullulanase activity, and wherein the variant has at least 85% but less than 100% sequence identity to a parent pullulanase selected from the group consisting of SEQ ID NO: 1, SEQ ID NO: 3, SEQ ID NO: 4, SEQ ID NO: 5.

4. The variant pullulanase of claim 1, comprising a substitution at a position corresponding to position 370 of SEQ ID NO: 1, wherein the variant pullulanase comprises serine in position 370 using SEQ ID NO: 1 for numbering, wherein the variant has pullulanase activity, and wherein the variant has at least 85% but less than 100% sequence identity to a parent pullulanase selected from the group consisting of SEQ ID NO: 1, SEQ ID NO: 3, SEQ ID NO: 4, SEQ ID NO: 5.

5. The variant pullulanase of claim 1, wherein the substitutions are selected from the group consisting of: K370S, F17Y, D77G, S103K, Q106W, A107D, A190I, V196T,C, T197I, T262V, Q279R, N283F, H321V, D367G,N, S375H, N382T, Q399N, N401D, S402Q, N411L, Y412F, F432V, Q434E, L435A, R443G, I446V, G459E, V460E, H479N, T486A, V, I490L, Q498R, V514A, T529L, S531R, A533I, N541D, A545I, L581F, N583D, Q595R, D649A, V665I, D688A, F700L, P709I, E804S, and G811R.

6. The variant pullulanase of claim 1 wherein thermostability is determined as relative activity after heat stress for 30 min at two different temperatures, using PHADEBAS assay.

7. The variant pullulanase of claim 1, wherein thermostability is determined as increased melting (denaturing) temperature compared to the parent pullulanase using TSA assay.

8. The variant pullulanase of claim 1, wherein thermoactivity is determined as relative activity determined at two different temperatures selected from the range of 70-86° C. using PHADEBAS assay.

9. The variant pullulanase claim 1, wherein the variant comprises combinations of substitutions and/or deletions selected from the group consisting of:
Q279R+K370S;
H321E+K370S;
K370S+V821*+S822*+P823*+D824*+H825*+G826*+K827*+K828*;
K370S+Q399N;
K370S+N401D;
K370S+F432V;
V196T+K370S;
V196C+K370S;
T197I+K370S;
K370S+V460E;
K370S+T486A;
K370S+T486V;
K370S+I490L;
K370S+V514A;
K370S+T529L;
K370S+S531R;
K370S+Q595R;
H321E+K370S+F432V;
K370S+F432V+V821*+S822*+P823*+D824*+H825*+G826*+K827*+K828*;
K370S+Q399N+F432V;
K370S+N401D+F432V;
V196T+K370S+F432V;
V196C+K370S+F432V;
T197I+K370S+F432V;
K370S+F432V+G459E;
K370S+F432V+T486A;
K370S+F432V+T486V;
V196T+K370S+F432V+T486A;
T197I+K370S+F432V+T486A;
V196T+T197I+K370S+F432V+T486A;
K370S+Q399N+F432V+T486A;
K370S+N401D+F432V+T486A;
K370S+Q399N+N401D+F432V+T486A;
K370S+S531R+F432V+T486A;
K370S+Q595R+F432V+T486A;
K370S+F432V+T486A+S531R+Q595R;
V196T+T197I+K370S+Q399N+N401D+F432V+T486A;
V196T+T197I+K370S+Q399N+N401D+F432V+T486A+Q595R;
T197I+K370S+N401D+F432V+T486A+S531R+Q595R;
T197I+K370S+N401D+F432V+T486A+S531R+Q595R+V821*+S822*+P823*+D824*+H825*+G826*+K827*+K828*;
T197I+K370S+Q399N+N401D+F432V+T486A+Q595R;
S103K+T197I+K370S+N401D+F432V+T486A+S531R+Q595R;
V196T+T197I+K370S+Q399N+N401D+F432V+T486V+Q595R;
T197I+K370S+N401D+F432V+T486V+S531R+Q595R;
V196T+T197I+K370S+Q399N+N401D+F432V+T486A+S531R+Q595R;
D77G+T197I+K370S+N401D+F432V+T486V+S531R+Q595R;
T197I+K370S+N401D+S402Q+F432V+T486V+S531R+Q595R;
T197I+N283F+K370S+N401D+F432V+T486V+S531R+Q595R;
T197I+N283F+K370S+N401D+S402Q+F432V+T486V+S531R+Q595R;
T197I+N283F+K370S+N401D+F432V+L435A+T486V+S531R+Q595R;
D77G+T197I+N283F+K370S+N401D+S402Q+F432V+T486V+S531R+Q595R;
T197I+N283F+K370S+N401D+S402Q+F432V+L435A+T486V+S531R+Q595R;
D77G+T197I+N283F+K370S+N401D+S402Q+F432V+L435A+T486V+S531R+Q595R;
T197I+N283F+K370S+N401D+S402Q+F432V+L435A+T486V+S531R+Q595R+D649A;
D77G+T197I+N283F+K370S+N401D+S402Q+F432V+L435A+T486V+S531R+Q595R+D649A;
D77G+Q106W+T197I+N283F+K370S+N401D+S402Q+F432V+L435A+T486V+S531R+Q595R;
D77G+A107D+T197I+N283F+K370S+N401D+S402Q+F432V+L435A+T486V+S531R+Q595R;
D77G+V196C+T197I+N283F+K370S+N401D+S402Q+F432V+L435A+T486V+S531R+Q595R;
D77G+T197I+N283F+K370S+N401D+S402Q+F432V+L435A+T486V+S531R+N583D+Q595R;
D77G+T197I+N283F+K370S+N401D+S402Q+F432V+L435A+T486V+S531R+Q595R+V821*+S822*+P823*+D824*+H825*+G826*+K827*+K828*;
D77G+T197I+N283F+K370S+N401D+S402Q+F432V+L435A+T486V+S531R+Q595R+D688A+V821*+S822*+P823*+D824*+H825*+G826*+K827*+K828*;
D77G+T197I+N283F+D367G+K370S+N401D+S402Q+F432V+L435A+T486V+S531R+Q595R+V821*+S822*+P823*+D824*+H825*+G826*+K827*+K828*;
D77G+T197I+N283F+D367N+K370S+N401D+S402Q+F432V+L435A+T486V+S531R+Q595R+V821*+S822*+P823*+D824*+H825*+G826*+K827*+K828*;
D77G+T197I+N283F+K370S+S375H+N401D+S402Q+F432V+L435A+T486V+S531R+Q595R+V821*+S822*+P823*+D824*+H825*+G826*+K827*+K828*;
D77G+T197I+N283F+K370S+N382T+N401D+S402Q+F432V+L435A+T486V+S531R+Q595R+V821*+S822*+P823*+D824*+H825*+G826*+K827*+K828*;
D77G+T197I+N283F+K370S+N401D+S402Q+N411L+F432V+L435A+T486V+S531R+Q595R+V821*+S822*+P823*+D824*+H825*+G826*+K827*+K828*;
D77G+T197I+N283F+K370S+N401D+S402Q+Y412F+F432V+L435A+T486V+S531R+Q595R+V821*+S822*+P823*+D824*+H825*+G826*+K827*+K828*;
D77G+T197I+N283F+K370S+N401D+S402Q+F432V+Q434E+L435A+T486V+S531R+Q595R+V821*+S822*+P823*+D824*+H825*+G826*+K827*+K828*;
D77G+T197I+N283F+K370S+N401D+S402Q+F432V+L435A+R443G+T486V+S531R+Q595R+V821*+S822*+P823*+D824*+H825*+G826*+K827*+K828*;
D77G+T197I+N283F+K370S+N401D+S402Q+F432V+L435A+I446V+T486V+S531R+Q595R+V821*+S822*+P823*+D824*+H825*+G826*+K827*+K828*;

D77G+T197I+N283F+K370S+N401D+S402Q+F432V+
L435A+T486V+Q498R+S531R+Q595R+V821*+
S822*+P823*+D824*+H825*+G826*+K827*+
K828*;
D77G+T197I+N283F+K370S+N401D+S402Q+F432V+
L435A+T486V+S531R+A533I+Q595R+V821*+
S822*+P823*+D824*+H825*+G826*+K827*+
K828*;
D77G+T197I+N283F+K370S+N401D+S402Q+F432V+
L435A+T486V+S531R+N541D+Q595R+V821*+
S822*+P823*+D824*+H825*+G826*+K827*+
K828*;
D77G+T197I+N283F+K370S+N401D+S402Q+F432V+
L435A+T486V+S531R+A545I+Q595R+V821*+
S822*+P823*+D824*+H825*+G826*+K827*+
K828*;
D77G+T197I+N283F+K370S+N401D+S402Q+F432V+
L435A+T486V+S531R+L581F+Q595R+V821*+
S822*+P823*+D824*+H825*+G826*+K827*+
K828*;
D77G+T197I+N283F+K370S+N401D+S402Q+F432V+
L435A+H479N+T486V+S531R+Q595R+D688A+
V821*+S822*+P823*+D824*+H825*+G826*+
K827*+K828*;
D77G+T197I+N283F+D367N+K370S+N401D+S402Q+
F432V+L435A+T486V+S531R+Q595R+D688A+
V821*+S822*+P823*+D824*+H825*+G826*+
K827*+K828*;
D77G+T197I+N283F+K370S+S375H+N401D+S402Q+
F432V+L435A+T486V+S531R+Q595R+D688A+
V821*+S822*+P823*+D824*+H825*+G826*+
K827*+K828*;
D77G+T197I+N283F+K370S+N401D+S402Q+Y412F+
F432V+L435A+T486V+S531R+Q595R+D688A+
V821*+S822*+P823*+D824*+H825*+G826*+
K827*+K828*;
D77G+T197I+N283F+K370S+N401D+S402Q+F432V+
L435A+T486V+S531R+A533I+Q595R+D688A+
V821*+S822*+P823*+D824*+H825*+G826*+
K827*+K828*;
D77G+T197I+N283F+K370S+N401D+S402Q+F432V+
L435A+T486V+S531R+L581F+Q595R+D688A+
V821*+S822*+P823*+D824*+H825*+G826*+
K827*+K828*;
D77G T197I N283F D367N K370S S375H N401D
S402Q F432V L435A T486V S531R Q595R D688A
V821*S822*P823*D824*H825*G826*K827*K828*;
D77G T197I N283F D367N K370S N401D S402Q
Y412F F432V L435A T486V S531R Q595R D688A
V821*S822*P823*D824*H825*G826*K827*K828*;
D77G T197I N283F D367N K370S N401D S402Q
F432V L435A T486V S531R A533I Q595R D688A
V821*S822*P823*D824*H825*G826*K827*K828*;
D77G T197I N283F D367N K370S N401D S402Q
F432V L435A T486V S531R L581F Q595R D688A
V821*S822*P823*D824*H825*G826*K827*K828*;
D77G T197I N283F K370S N401D S402Q F432V
L435A T486V S531R Q595R V665I
V821*S822*P823*D824*H825*G826*K827*K828*;
D77G T197I N283F K370S N401D S402Q F432V
L435A T486V S531R Q595R F700L
V821*S822*P823*D824*H825*G826*K827*K828*;
D77G T197I N283F K370S N401D S402Q F432V
L435A T486V S531R Q595R P709I
V821*S822*P823*D824*H825*G826*K827*K828*;
D77G T197I N283F D367N K370S S375H N401D
S402Q Y412F F432V L435A T486V S531R Q595R
D688A
V821*S822*P823*D824*H825*G826*K827*K828*;
D77G T197I N283F D367N K370S S375H N401D
S402Q F432V L435A T486V S531R A533I Q595R
D688A
V821*S822*P823*D824*H825*G826*K827*K828*;
D77G T197I N283F D367N K370S S375H N401D
S402Q Y412F F432V L435A T486V S531R A533I
L581F Q595R D688A
V821*S822*P823*D824*H825*G826*K827*K828*;
D77G T197I N283F H321V D367N K370S S375H
N401D S402Q Y412F F432V Q434E L435A T486V
S531R A533I L581F Q595R D688A
V821*S822*P823*D824*H825*G826*K827*K828*;
D77G T197I N283F H321V D367N K370S S375H
N401D S402Q Y412F F432V L435A T486V Q498R
S531R A533I L581F Q595R D688A
V821*S822*P823*D824*H825*G826*K827*K828*;
D77G T197I N283F H321V D367N K370S S375H
N401D S402Q Y412F F432V L435A T486V S531R
A533I L581F Q595R D688A F700L
V821*S822*P823*D824*H825*G826*K827*K828*;
D77G T197I N283F H321V D367N K370S S375H
N401D S402Q Y412F F432V Q434E L435A T486V
Q498R S531R A533I L581F Q595R D688A F700L
V821*S822*P823*D824*H825*G826*K827*K828*;
F17Y D77G T197I N283F K370S N401D S402Q F432V
L435A T486V S531R Q595R
V821*S822*P823*D824*H825*G826*K827*K828*;
D77G T197I N283F K370S N401D S402Q F432V
L435A T486V S531R Q595R E804S
V821*S822*P823*D824*H825*G826*K827*K828*;
D77G T197I N283F K370S N401D S402Q F432V
L435A T486V S531R Q595R G811R
V821*S822*P823*D824*H825*G826*K827*K828*;
D77G T197I N283F H321V K370S S375H N401D
S402Q Y412F F432V Q434E L435A H479N T486V
Q498R S531R A533I L581F Q595R D688A F700L
V821*S822*P823*D824*H825*G826*K827*K828*;
D77G A190I T197I N283F K370S S375H N401D S402Q
Y412F F432V Q434E L435A H479N T486V Q498R
S531R A533I L581F Q595R D688A F700L
V821*S822*P823*D824*H825*G826*K827*K828*;
D77G T197I T262V N283F K370S S375H N401D
S402Q Y412F F432V Q434E L435A H479N T486V
Q498R S531R A533I L581F Q595R D688A F700L
V821*S822*P823*D824*H825*G826*K827*K828*;
and
D77G A190I T197I N283F H321V D367N K370S S375H
N401D S402Q Y412F F432V Q434E L435A T486V
Q498R S531R A533I L581F Q595R D688A F700L
V821*S822*P823*D824*H825*G826*K827*K828*.

10. The variant pullulanase claim 1, comprising the substitutions N222P+Q252A+Q256R+N368G+N393A+Q431E+N610R+G624S+T631S+S632C, and optionally L432F.

11. The variant pullulanase of claim 1, comprising the substitutions N222P+Q252A+Q256R+N368G+N393A+Q431E+N610R+G624S+T631S+S632C+N20G+Y28K+H80Y+Q187R+E310A+D311K+Q387L+Q459G+D586S+E699R+S798R, and optionally L432F.

12. The variant pullulanase of claim 1, comprising the deletions P30*+V31*+N32*, and optionally Q29G.

13. The variant pullulanase of claim 1, comprising the modifications Q29G+P30*+V31*+N32*+D57N+D58P+

A195G+N202K+A345P+F456W+E560R, and optionally one, two, three, four or five of N197T, M402S, I460V, N479H, I514V.

14. The variant pullulanase of claim 1, comprising the modifications N222P+Q252A+Q256R+N368G+N393A+ Q431E++N610R+G624S+T631S+S632C+N20G+Y28K+ H80Y+Q187R+E310A+D311K+Q387L+Q459G+D586S+ E699R+S798R+Q29G+P30*+V31*+N32*+D57N+D58P+ A195G+N202K+A345P+F456W+E560R, and optionally one, two, three, four, five or six of L432F, N197T, M402S, N479H, I460V, I514V.

15. The variant of claim 1, wherein the variant comprises the substitutions X370S+X432V, particularly K370S+L, F432V, and optionally X492A,S.

16. The variant of claim 1, wherein the variants has an increase in thermo-activity relative to the pullulanase disclosed as SEQ ID NO: 3, of at least 5%, at least 10%, at least 20%, at least 25%, at least 30%, at least 35%, at least 40%, at least 50%, at least 60%, at least 70%, at least 80%, at least 90%, at least 100%, after enzymatic reaction of maltodextrin 2 hours at 85° C. or 30 min 91° C., and subsequent determination of digested maltodextrin fraction by PAH-BAH assay at 55° C.

17. The variants of claim 1, wherein the increase in thermo-stability determined as increased melting (denaturing) temperature compared to the parent pullulanase disclosed in SEQ ID NO: 3 using TSA assay is at least 0.3 degrees C., at least 0.4 degrees C., at least 0.5 degrees C., at least 0.6 degrees C., at least 0.8 degrees C., at least 1.0 degrees C., at least 1.2 degrees C., at least 1.5 degrees C., at least 2.0 degrees C., at least 2.5 degrees C., at least 3.0 degrees C., at least 3.5 degrees C., at least 4.0 degrees C., at least 4.5 degrees C., at least 5.0 degrees C.

18. A polynucleotide encoding the variant pullulanase claim 1.

19. A nucleic acid construct or expression vector comprising the polynucleotide of claim 18 operably linked to one or more control sequences that direct the production of the polypeptide in an expression host.

20. A recombinant host cell comprising the polynucleotide of claim 18 operably linked to one or more control sequences that direct the production of the polypeptide.

21. A composition comprising the variant pullulanase of claim 1 and a stabilizer.

22. A method of producing a variant pullulanase according to claim 1, comprising cultivating the host cell of claim 20 under conditions conducive for production of the polypeptide.

23. A process for producing a syrup from starch-containing material comprising the steps of:
  a) liquefying the starch-containing material at a temperature above the initial gelatinization temperature using an alpha-amylase and a variant pullulanase of claim 1;
  b) saccharifying using a glucoamylase.

24. A process for producing fermentation products from starch-containing material comprising the steps of:
  a) liquefying the starch-containing material at a temperature above the initial gelatinization temperature using an alpha-amylase and a variant pullulanase of claim 1;
  b) saccharifying using a glucoamylase;
  c) fermenting using a fermenting organism.

25. A method of producing a brewer's wort comprising adding to a mash, a pullulanase of claim 1.

* * * * *